US012260604B2

(12) United States Patent
Hamada

(10) Patent No.: US 12,260,604 B2
(45) Date of Patent: Mar. 25, 2025

(54) MATCHING SUPPORT APPARATUS, MATCHING SUPPORT METHOD, AND COMPUTER-READABLE RECORDING MEDIUM

(71) Applicant: NEC Corporation, Tokyo (JP)

(72) Inventor: Yasushi Hamada, Tokyo (JP)

(73) Assignee: NEC CORPORATION, Tokyo (JP)

( * ) Notice: Subject to any disclaimer, the term of this patent is extended or adjusted under 35 U.S.C. 154(b) by 429 days.

(21) Appl. No.: 17/636,142

(22) PCT Filed: Oct. 13, 2019

(86) PCT No.: PCT/JP2019/042674
§ 371 (c)(1),
(2) Date: Feb. 17, 2022

(87) PCT Pub. No.: WO2021/084661
PCT Pub. Date: May 6, 2021

(65) Prior Publication Data
US 2022/0292799 A1 Sep. 15, 2022

(51) Int. Cl.
*G06V 10/22* (2022.01)
*G06V 40/16* (2022.01)

(52) U.S. Cl.
CPC .......... *G06V 10/235* (2022.01); *G06V 40/172* (2022.01)

(58) Field of Classification Search
CPC ..... A61B 5/1171; G06F 21/32; G06V 10/235; G06V 40/171; G06V 40/172; H04L 63/0861
See application file for complete search history.

(56) References Cited

U.S. PATENT DOCUMENTS 10,929,849 B2 * 2/2021 Remillet ................ G06T 17/20
2003/0223622 A1 12/2003 Simon et al.
(Continued)

FOREIGN PATENT DOCUMENTS

CO 2017008821 A2 11/2017
EP 1372109 A2 12/2003
(Continued)

OTHER PUBLICATIONS

International Search Report for PCT Application No. PCT/JP2019/042674, mailed on Jan. 7, 2020.
(Continued)

*Primary Examiner* — Ruiping Li

(57) ABSTRACT

A matching support apparatus includes a first display information generation unit that generates first display information for displaying, on the screen of a display device, a first display region for displaying an image including the face of a person targeted for matching captured using an image capturing apparatus, a second display information generation unit that generates second display information for displaying, on the screen of the display device 30, a second display region for displaying a reference face development image generated based on three-dimensional data of a head serving as a reference, and a user interface display information generation unit that generates first user interface display information for displaying, on the screen of the display device 30, a second user interface to be used in an operation for enabling a user to designate, in the second display region, a feature region of the person targeted for matching visible on the skin surface of the person targeted for matching.

12 Claims, 12 Drawing Sheets

(56) References Cited

U.S. PATENT DOCUMENTS

| | | | |
|---|---|---|---|
| 2009/0028380 A1* | 1/2009 | Hillebrand | G06T 7/33 |
| | | | 382/100 |
| 2016/0132670 A1 | 5/2016 | Salama et al. | |
| 2018/0316906 A1 | 11/2018 | Nobori et al. | |
| 2019/0080066 A1 | 3/2019 | Van Os et al. | |
| 2019/0154439 A1 | 5/2019 | Binder | |

FOREIGN PATENT DOCUMENTS

| | | |
|---|---|---|
| JP | 2005-275605 A | 10/2005 |
| JP | 2007-304857 A | 11/2007 |
| JP | 2008-152581 A | 7/2008 |
| JP | 2011-039869 A | 2/2011 |
| JP | 2018-190402 A | 11/2018 |
| WO | 2017/149526 A2 | 9/2017 |

OTHER PUBLICATIONS

Extended European Search Report for EP Application No. 19950582.7, dated on Sep. 29, 2022.
IN Office Action for IN Application No. 202217013881, mailed on Aug. 16, 2022 with English Translation.
English translation of Written opinion for PCT Application No. PCT/JP2019/042674, mailed on Jan. 7, 2020.
CO Office Action including Search Report for Colombian Patent Application No. NC2022/0002542, issued on Jul. 24, 2024 with English Translation.

* cited by examiner

MATCHING SUPPORT APPARATUS, MATCHING SUPPORT METHOD, AND COMPUTER-READABLE RECORDING MEDIUM

This application is a National Stage Entry of PCT/JP2019/042674 filed on Oct. 30, 2019, the contents of all of which are incorporated herein by reference, in their entirety.

TECHNICAL FIELD

The technical field relates to a matching support apparatus and a matching support method for supporting matching, and further relates to a computer-readable recording medium that includes a program recorded thereon for realizing the apparatus and method.

BACKGROUND ART

Matching apparatuses have been proposed that perform matching using the face image of a targeted person and preregistered face images, and specify the targeted person based on a matching result.

For example, as a related technology, Patent Document 1 discloses an authentication system that is able to perform authentication with high accuracy in the case of authenticating the identity of a person. According to the authentication system of Patent Document 1, a feature region corresponding to a discrete feature site (mole, scar, wrinkle) is automatically detected from an image captured of the person targeted for authentication, a feature amount of the detected feature region is recognized, and authentication is executed using the recognized feature amount.

LIST OF RELATED ART DOCUMENTS

Patent Document

Patent Document 1: Japanese Patent Laid-Open Publication No. 2007-304857

SUMMARY

Technical Problems

However, with the authentication system of Patent Document 1, preregistered face images are used, and thus matching may not be possible in the case where the orientation of the face in the registered face images is different from the orientation of the face of the targeted person in the captured image. For example, in the case where the face of the targeted person in the captured image is not facing forward, the apparent position of the discrete feature site changes due to the undulations of the face, and thus a forward-facing face image must always be used.

Accordingly, in the case where an image of a face that is not facing forward is used, performing matching using the face image will be difficult. In view of this, there are calls to also be able to designate a feature region corresponding to a discrete feature site, when using an image of a face that is not facing forward.

An example object is to provide a matching support apparatus, a matching support method and a computer-readable recording medium with which a feature visible on the skin surface of the face of a person targeted for matching can be designated, according to the orientation of the face in a captured image.

Solution to the Problems

A matching support apparatus according to an example aspect includes:

a first display information generation unit that generates first display information for displaying, on a screen of a display device, a first display region for displaying an image including a face of a person targeted for matching captured using an image capturing apparatus;

a second display information generation unit that generates second display information for displaying, on the screen of the display device, a second display region for displaying a reference face development image generated based on three-dimensional data of a head serving as a reference; and a user interface display information generation unit that generates first user interface display information for displaying, on the screen of the display device, a first user interface to be used in an operation for enabling a user to designate, in the second display region, a feature region indicating a facial feature of the person targeted for matching visible on a skin surface of the person targeted for matching.

Also, a matching support method according to an example aspect includes:

generating first display information for displaying, on a screen of a display device, a first display region for displaying an image including a face of a person targeted for matching captured using an image capturing apparatus;

generating second display information for displaying, on the screen of the display device, a second display region for displaying a reference face development image generated based on three-dimensional data of a head serving as a reference; and generating first user interface display information for displaying, on the screen of the display device, a first user interface to be used in an operation for enabling a user to designate, in the second display region, a feature region indicating a facial feature of the person targeted for matching visible on a skin surface of the person targeted for matching.

Furthermore, a computer-readable recording medium according to an example aspect invention includes a program recorded thereon, the program including instruction that cause a computer to carry out:

generating first display information for displaying, on a screen of a display device, a first display region for displaying an image including a face of a person targeted for matching captured using an image capturing apparatus;

generating second display information for displaying, on the screen of the display device, a second display region for displaying a reference face development image generated based on three-dimensional data of a head serving as a reference; and generating first user interface display information for displaying, on the screen of the display device, a first user interface to be used in an operation for enabling a user to designate, in the second display region, a feature region indicating a facial feature of the person targeted for matching visible on a skin surface of the person targeted for matching.

Advantageous Effects

According to described above, a feature visible on the skin surface of the face of a person targeted for matching can be designated, according to the orientation of the face in a captured image.

EXAMPLE EMBODIMENTS

Example Embodiment

Figure 1:
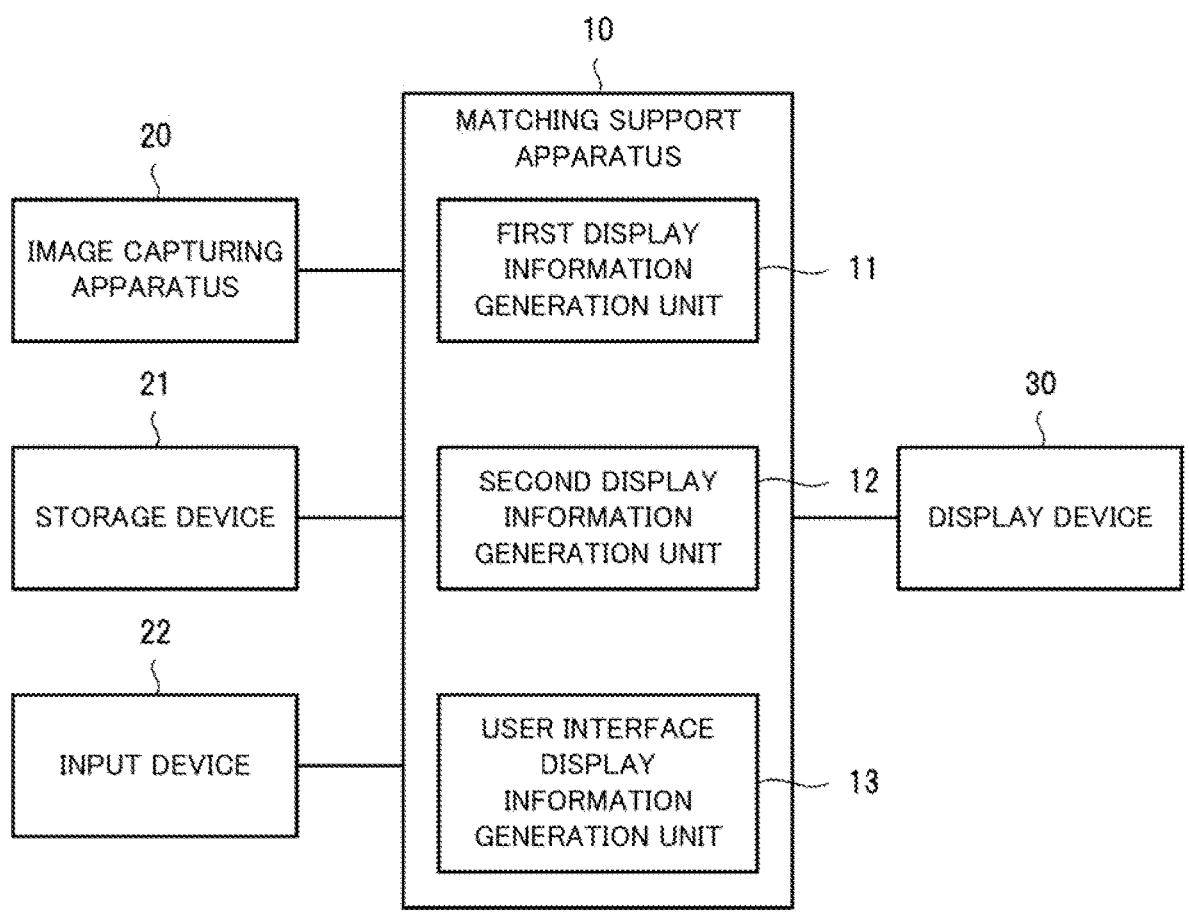
FIG. 1 is a diagram for describing an example of a matching support apparatus.
Figure 2:
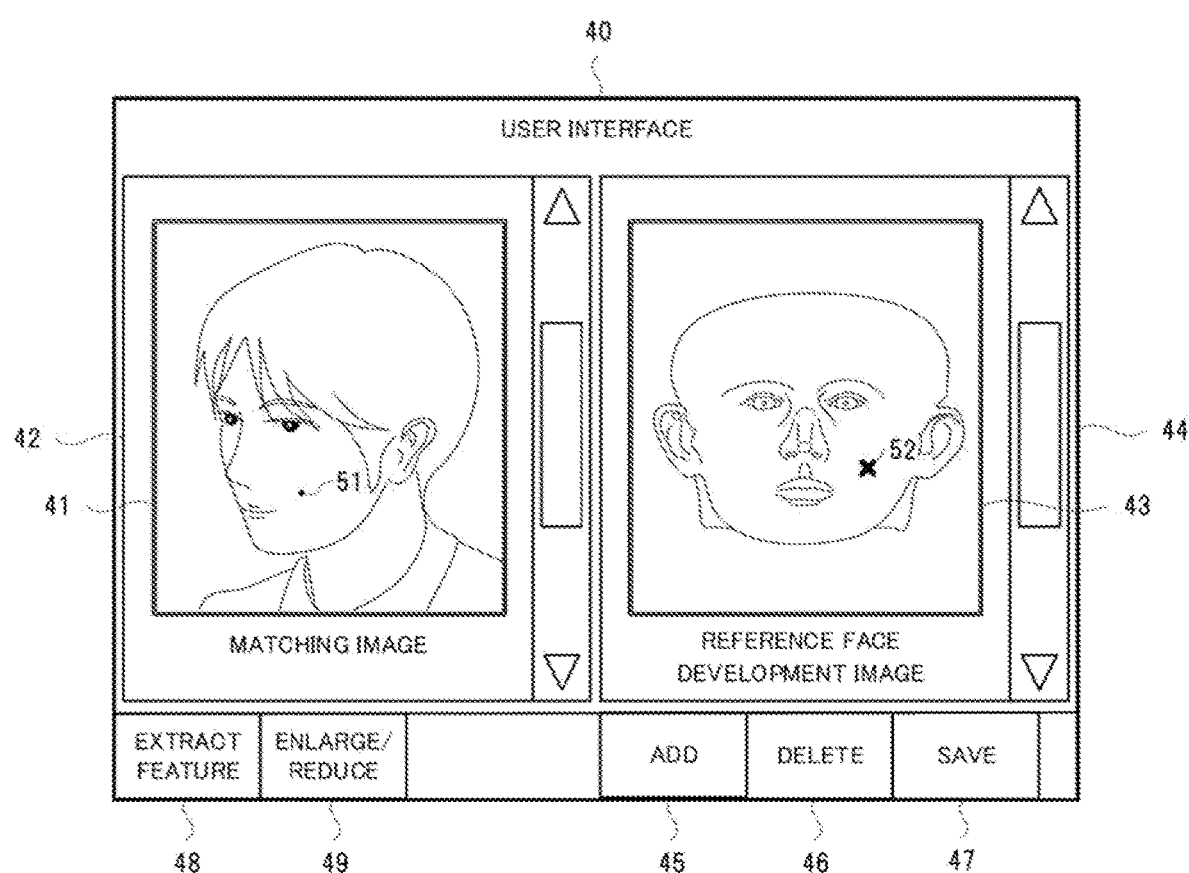
FIG. 2 is a diagram for describing a user interface that is used in matching support.

Hereinafter, an example embodiment will be described with reference to FIGS. 1 to 12.
[Apparatus Configuration]
Initially, the configuration of a matching support apparatus 10 in this example embodiment will be described using FIGS. 1 and 2. FIG. 1 is a diagram for describing an example of the matching support apparatus. FIG. 2 is a diagram for describing a user interface that is used in matching support.

The matching support apparatus 10 shown in FIG. 1 is an apparatus with which a feature visible on the skin surface of the face of a person targeted for matching can be designated, according to the orientation of the face in a captured image. Also, as shown in FIG. 1, the matching support apparatus 10 has a first display information generation unit 11, a second display information generation unit 12 and a user interface display information generation unit 13. Furthermore, as shown in FIG. 1, the matching support apparatus 10 is connected to an image capturing apparatus 20, a storage device 21, an input device 22 and a display device 30.

Of these, the first display information generation unit 11 generates first display information for displaying, on the screen of the display device 30, a first display region for displaying a matching image that includes the face of the person targeted for matching captured using the image capturing apparatus 20.

The first display region is an area for displaying a matching image 41 on a user interface 40 shown in FIG. 2, for example. The matching image 41 is, for instance, a frame image of a still image or moving image. Note that, in the example in FIG. 2, the matching image 41 is displayed in a window 42. The configuration of the display screen is, however, not limited to that in FIG. 2.

The second display information generation unit 12 generates second display information for displaying, on the screen of the display device 30, a second display region for displaying a reference face development image generated based on three-dimensional data of a head serving as a reference.

The reference head is, for instance, a head created by CG (Computer Graphics) based on data of one or more heads measured or captured in the past. The reference head may also be created based on the head of a specific person measured or captured in the past.

The second display region is an area for displaying a reference face development image 43 on the user interface 40 shown in FIG. 2, for example. The reference face development image 43 is a development image of a face cylindrically projected by executing UV development processing, for example, using the three-dimensional data of the reference head stored in the storage device 21 in advance. The creation of the development image of a face is, however, not limited to the above-described cylindrical projection. Note that, in the example in FIG. 2, the reference face development image 43 is displayed in a window 44. The configuration of the display screen is, however, not limited to that in FIG. 2.

The user interface display information generation unit 13 generates first user interface display information for displaying, on the screen of the display device 30, a first user interface to be used in an operation for enabling the user to designate, in the second display region, a feature region indicating a facial feature of the person targeted for matching visible on the skin surface of the person targeted for matching.

Features on a person's face are sites indicating features of the person that are visible on the skin surface such as moles, freckles, tattoos, birthmarks, wrinkles, dimples, scars, warts, lumps, rough skin and discolored skin patches, for example. In the example in FIG. 2, there is a mole 51 on the left cheek of the person captured in the matching image 41, and thus this mole 51 is a feature.

The feature region is a region corresponding to a feature on the person's face recognized by the user, with a marker that the user attaches to the reference face development image after having recognized the feature. In the example in FIG. 2, the region corresponding to the marker (x) on the reference face development image 43 is a feature region 52. Note that a region of a person's face in which there are no features may also be taken as a feature region.

In the example in FIG. 2, the first user interface corresponds to the user interface 40. For example, in the case where the feature region 52 is drawn (designated) using the user interface 40 and the input device 22, which is a physical user interface such as a mouse, touch panel or keyboard, the drawn feature region 52 is added to the reference face development image 43 when an "add" button 45 displayed on the user interface 40 is selected.

In this way, in this example embodiment, by the user viewing the matching image 41 and designating the feature region 52 on the reference face development image 43, matching support leading to specification of the person targeted for matching can be provided using the designated feature region 52, even if the person in the matching image 41 is not facing forward. Matching support is processing for selecting a person having a feature in the same position as the person targeted for matching, using the feature region 52 designated on the reference face development image 43.

Also, by the feature region 52 being designated utilizing the reference face development image 43, the influence of the undulations of the face arising from a change in the face orientation can be reduced, thus enabling the user to easily designate the feature region 52 corresponding to the mole 51 on the reference face development image 43, even if the apparent position of the mole 51 changes.

[System Configuration]

Figure 3:
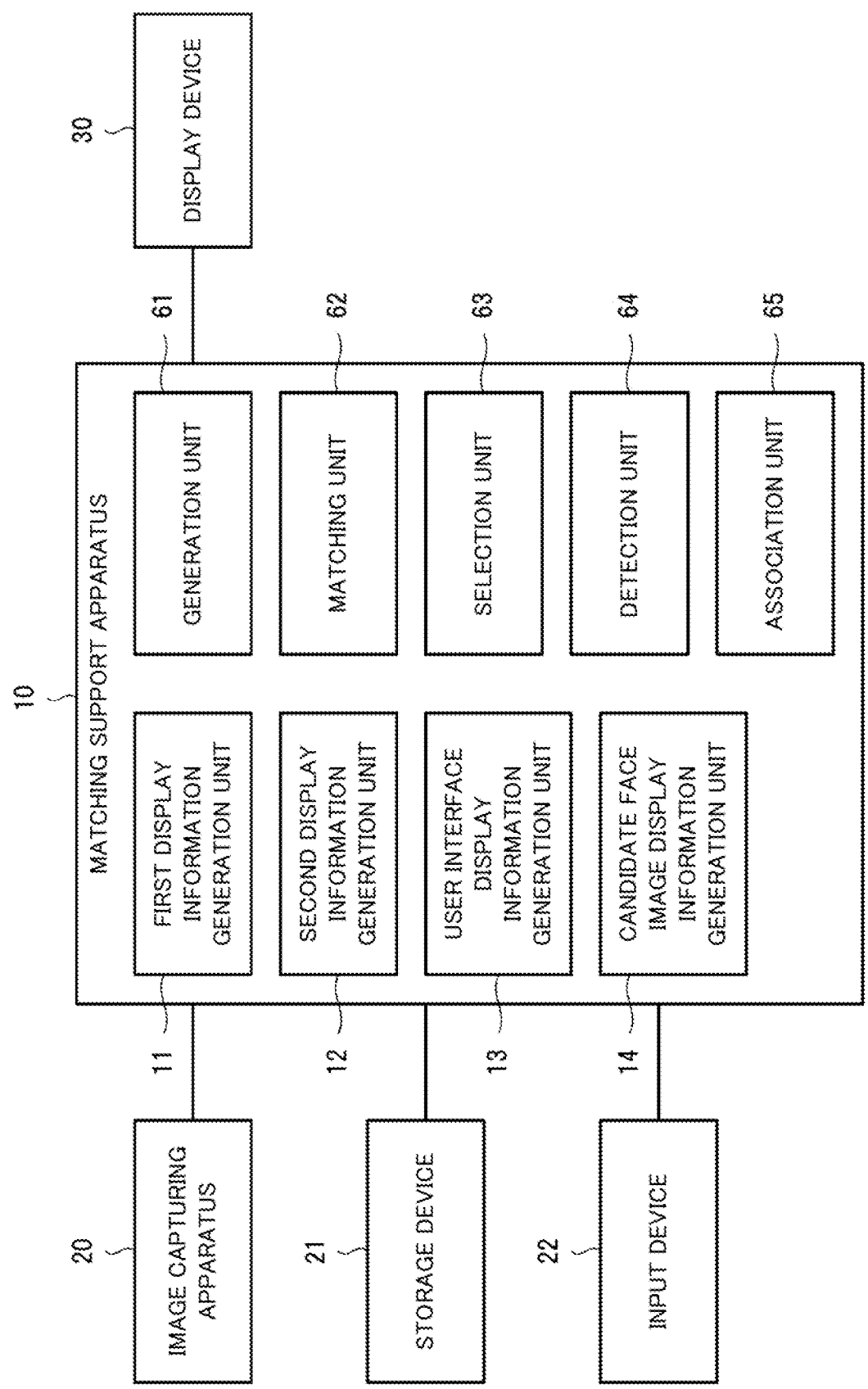
FIG. 3 is a diagram for describing an example of a system having the matching support apparatus.

Next, the configuration of the matching support apparatus 10 in this example embodiment will be described more specifically using FIG. 3. FIG. 3 is a diagram for describing an example of a system having the matching support apparatus.

As shown in FIG. 3, the system in this example embodiment has the matching support apparatus 10, the image capturing apparatus 20, the storage device 21, the input device 22 and the display device 30. For example, the system is conceivably a monitoring system or an authentication system. Also, the matching support apparatus 10 in FIG. 3 has a candidate face image display information generation unit 14, a generation unit 61, a matching unit 62, a selection unit 63, a detection unit 64 and an association unit 65, in addition to the first display information generation unit 11, the second display information generation unit 12 and the user interface display information generation unit 13.

The system will now be described.

The matching support apparatus 10 is an information processing apparatus such as a server computer, personal computer or mobile terminal equipped with a CPU (Central Processing Unit), an FPGA (Field-Programmable Gate Array) or both thereof, for example.

The image capturing apparatus 20 is an apparatus for capturing an image of the face of the person targeted for matching. Specifically, the image capturing apparatus 20 transmits the captured image to the matching support apparatus 10 via a communication network. The image capturing apparatus 20 is an image capturing apparatus such as a camera, for example.

The storage device 21 stores the three-dimensional data of the reference head described above and matching information. The matching information is information in which a face development image for use in matching is associated with a feature region for use in matching. The matching-use face development image is a face development image generated based on the three-dimensional data of the head of each of a plurality of persons registered in advance. The matching-use feature region is a feature region indicating a feature visible on the skin surface of the head of each of the plurality of persons registered in advance. Note that the storage device 21 may also store a reference face development image, a reference face three-dimensional image or both thereof in advance.

Specifically, in the case of displaying the reference face development image in the second display region, the storage device 21 transmits the three-dimensional data of the reference head to the matching support apparatus 10 via the communication network. Note that, in the case where a reference face development image is stored, the storage device 21 transmits the reference face development image to the matching support apparatus 10.

Also, in the case where a person to serve as a candidate is selected, the storage device 21 transmits the matching information in which the matching-use face development image and matching-use feature region corresponding to the selected person are associated with each other to the matching support apparatus 10 via the communication network.

Note that the storage device 21 is a storage device such as a database, for example. Also, information such as the three-dimensional data of the reference head and matching information described above may be stored separately in a plurality of storage devices. Also, the storage device 21 may be provided inside the matching support apparatus 10 or may be provided externally thereto.

The input device 22 is a physical user interface such as a mouse, a touch panel or a keyboard, for example. Specifically, the input device 22 is used by the user when providing matching support using a user interface displayed on the display device 30.

The display device 30 acquires various display information and displays generated images and the like on the screen, based on the acquired display information. The display device 30 is a device that uses liquid crystals, organic EL (Electroluminescence) or CRTs (Cathode Ray Tubes), for example. Furthermore, the display device 30 may also include an audio output device such as a speaker. Note that the display device 30 may also be a printing device such as a printer.

The matching support apparatus will now be described.

The first display information generation unit 11 generates first display information for displaying, on the screen of the display device 30, a first display region for displaying a matching image captured using the image capturing apparatus 20. Specifically, the first display information generation unit 11 acquires an image of a person captured by the image capturing apparatus 20. Then, the first display information generation unit 11 generates first display information for displaying, on the screen of the display device 30, a matching image 41 such as shown in FIG. 2, based on the acquired image. Thereafter, the first display information generation unit 11 transmits the first display information to the display device 30.

Note that a configuration may be adopted in which only a frame image in which a feature is readily visible is used as the matching image. Also, a frame image in which a feature that was not visible until the orientation of the face changed is detected may be used as the matching image.

The second display information generation unit 12 generates second display information for displaying, on the screen of the display device 30, a second display region for displaying a reference face development image, based on the three-dimensional data of the reference head. Specifically, the second display information generation unit 12 acquires the three-dimensional data of the reference head from the storage device 21.

Then, the second display information generation unit 12 generates a reference face development image using the three-dimensional data of the reference head. Then, the second display information generation unit 12 generates second display information for displaying, on the screen of the display device 30, a reference face development image 43 such as shown in FIG. 2, based on the generated reference face development image. Thereafter, the second display information generation unit 12 transmits the second display information to the display device 30. Note that, in the case where a reference face development image is stored in the storage device 21, the second display information generation unit 12 may acquire the reference face development image directly from the storage device 21.

The user interface display information generation unit 13 generates first user interface display information for displaying, on the screen of the display device 30, a first user interface for enabling the user to designate a feature region in the second display region with reference to the first display region. Specifically, the user interface display information generation unit 13 displays a user interface 40 such as shown in FIG. 2 as the first user interface to enable the user to designate a feature region on the reference face development image.

Note that the user may designate a plurality of feature regions on the reference face development image, while viewing one matching image. Also, the user may designate one or more feature regions on the reference face development image, while viewing a plurality of matching images (frame images) in which the face is oriented differently. For example, the user may designate one or more feature regions on the reference face development image, while viewing a plurality of matching images in which the face is oriented differently. This results in feature regions being positioned accurately and enables the number of feature regions to be increased, thus improving matching accuracy.

Also, as shown in FIG. 2, it is conceivable to provide an "add" button 45, a "delete" button 46, a "save" button 47, an "extract feature" button 48 and an "enlarge/reduce" button 49, for example. When the "add" button 45 is selected, the feature region 52 drawn on the reference face development image 43 can be added. When the "delete" button 46 is selected, the feature region 52 drawn on the reference face development image 43 can be deleted. When the "save" button 47 is selected, feature information (e.g., texture information, position information, size information, shape information, feature type information indicating the type of feature, etc.) relating to the designated feature region 52 is stored in a storage unit. When the "extract feature" button 48 is selected, a feature is automatically extracted from the matching image 41. When the "enlarge/reduce" button 49 is selected, display of the matching image 41 or reference face development image 43 that is selected is enlarged or reduced. The editing functions are, however, not limited to the above-described functions.

In the case where a feature region indicating a facial feature of the person targeted for matching visible on the skin surface of the person targeted for matching is designated, using the second display region, displayed on the screen of the display device 30, that is for displaying the reference face development image generated based on the three-dimensional data of the reference head, the generation unit 61 generates feature information relating to that feature region.

Specifically, in the case where one or more feature regions are designated on the reference face development image, using the first user interface, the generation unit 61, first, generates feature information for each designated feature region. Thereafter, the generation unit 61 outputs the feature information to the matching unit 62.

In the example in FIG. 2, in the case where the feature region 52 is designated on the reference face development image 43 using the user interface 40, the generation unit 61 generates feature information of the designated feature region 52.

The matching unit 62 matches the feature information against matching information in which a matching-use face development image and matching-use feature region for each person registered in advance are associated with each other. Specifically, the matching unit 62, first, acquires feature information from the generation unit 61. Then, the matching unit 62 executes matching processing, with reference to the respective matching information stored in the storage device 21 using the acquired feature information, and calculates a matching result. Thereafter, the matching unit 62 associates the matching information with the calculated matching result.

The matching processing involves calculating a matching index (score) as a matching result, using a value indicating the approximateness of the position of the designated feature region to the position of the matching-use feature region, or a deviation (distance) between the position of the designated feature region and the position of the matching-use feature region, or a combination thereof, for example. Furthermore, in the case where a plurality of feature regions are designated, the matching index may be calculated using the interpositional relationship between the plurality of feature regions and the interpositional relationship between the plurality of matching-use feature regions.

The Euclidean distance between the two position coordinates of the designated feature region and the matching-use feature region, the similarity obtained through normalized correlation of texture information of the two feature regions, or the overlapping area of the two feature regions, for example, can be used as the matching index.

The selection unit 63 selects a person to serve as a candidate based on a matching result. Specifically, the selection unit 63 selects matching information whose matching index is greater than or equal to a threshold value set in advance. Then, the selection unit 63 outputs the selected matching information to the candidate face image display information generation unit 14.

In the case where the feature region designated using the first user interface is matched against matching information in which a matching-use face development image and matching-use feature region for each person registered in advance are associated with each other, and a candidate person is selected based on a matching result, the candidate face image display information generation unit 14 generates candidate face image display information for displaying, on the screen of the display device 30, the matching-use face development image corresponding to the selected candidate person together with the matching-use feature region.

Figure 4:
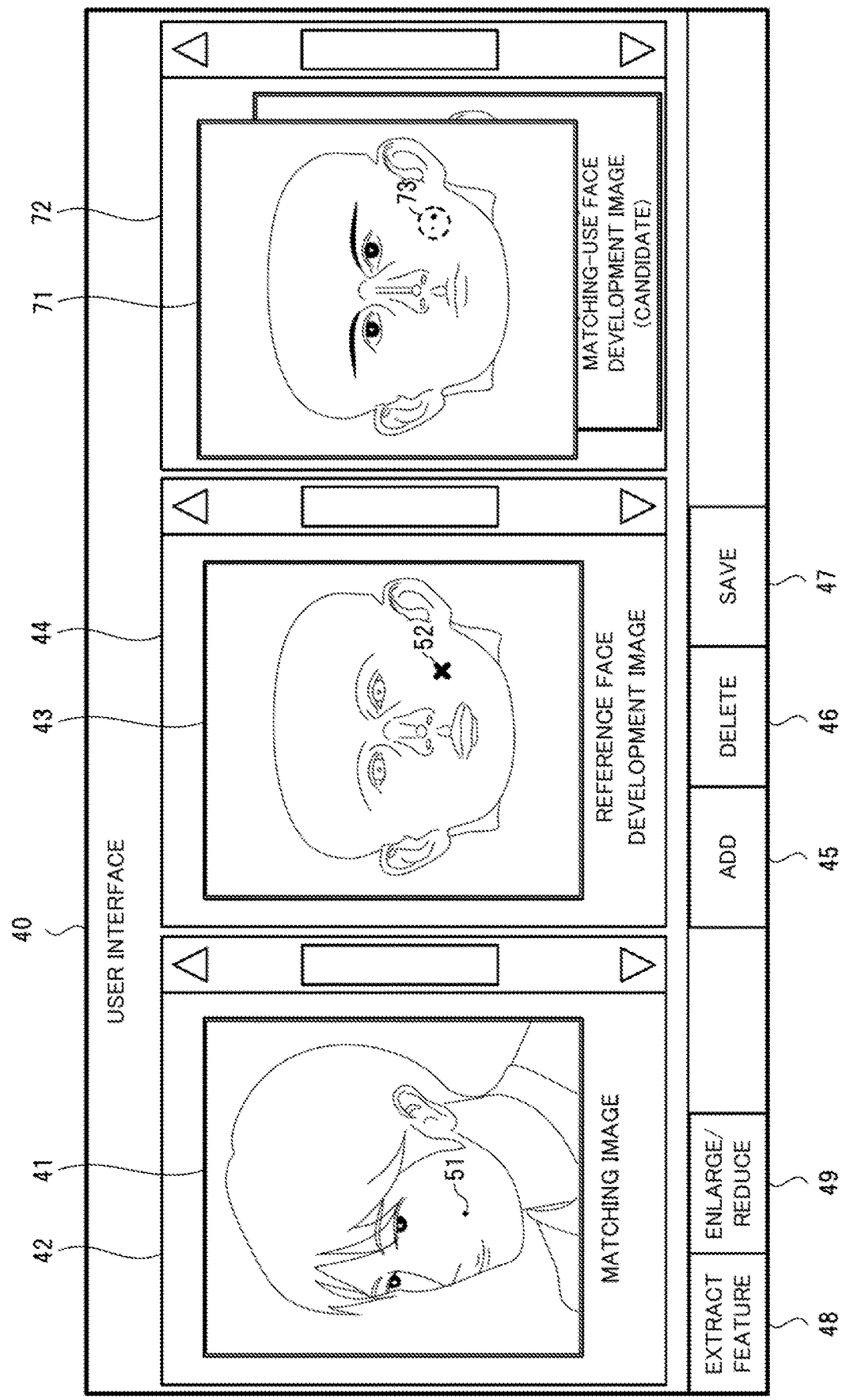
FIG. 4 is a diagram for describing an example of candidate face image display.

A specific description will now be given using FIG. 4. FIG. 4 is a diagram for describing an example of candidate face image display.

In the case where a candidate person is selected by the selection unit 63 based on a matching result of the matching unit 62, the candidate face image display information generation unit 14, first, acquires, from the storage device 21, the matching information in which the matching-use face development image and matching-use feature region corresponding to the selected candidate person are associated with each other.

Then, the candidate face image display information generation unit 14 generates candidate face image display information for displaying, on the screen of the display device 30, a matching-use face development image 71 and matching-use feature region 73 such as shown in a window 72 in FIG. 4, based on the acquired matching information. Thereafter, the candidate face image display information generation unit 14 transmits the candidate face image display information to the display device 30.

Note that, in the case where there are a plurality of candidate persons, the matching-use face development images are displayed in order, according to the matching results. For example, the matching-use face development images are displayed in descending order of matching indices (scores) indicated by the matching results.

The detection unit 64 automatically detects a feature region from an image, displayed on the screen of the display device 30, that includes the face of the person targeted for matching. Specifically, the detection unit 64 automatically detects a feature region corresponding to a feature on the person's face (e.g., feature of the person visible on the skin surface such as a mole, freckles, tattoo, birthmark, wrinkles, dimple, scar, wart, lump, skin roughness, discolored skin patch, etc.), using a matching image. Use of a technique such as segmentation processing is conceivable for detecting a feature region.

The association unit 65 may automatically associate the position of the detected feature region with a corresponding position on the reference face development image. Association may involve automatically associating the position of the detected feature region with a corresponding position on the reference face development image on the basis of the relative positional relationship between parts of the face such as the eyes, nose and mouth, for example.

[Apparatus Operations]

Figure 5:
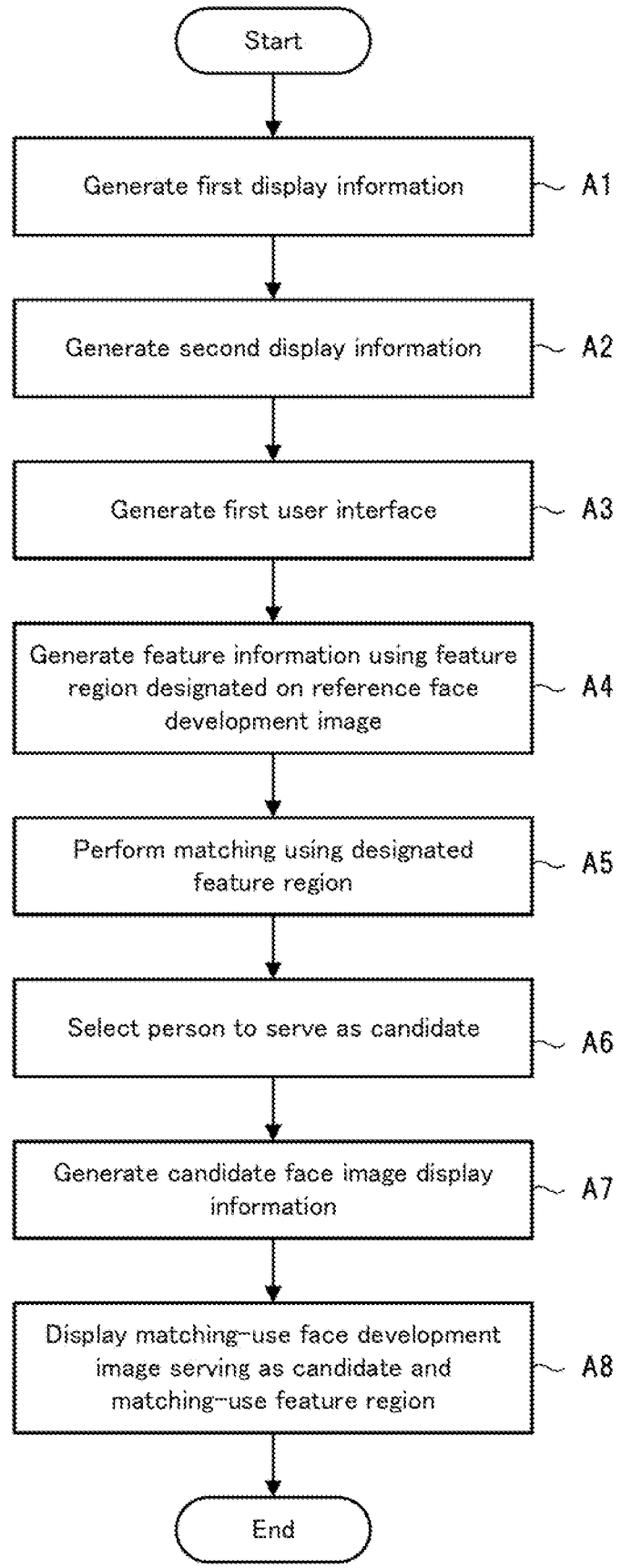
FIG. 5 is a diagram for describing an example of operations of the matching support apparatus.

Next, operations of the matching support apparatus in the example embodiment will be described using FIG. 5. FIG. 5 is a diagram for describing an example of operations of the matching support apparatus. In the following description, FIGS. 1 to 4 will be referred to as appropriate. Also, in this example embodiment, a matching support method is implemented by operating the matching support apparatus. Therefore, a description of the matching support method in this example embodiment is replaced by the following description of operations of the matching support apparatus.

As shown in FIG. 5, initially, the first display information generation unit 11 generates first display information for displaying, on the screen of the display device 30, a first display region for displaying a matching image captured using the image capturing apparatus 20 (step A1). Specifically, in step A1, the first display information generation unit 11 acquires an image of a person captured by the image capturing apparatus 20.

Then, in step A1, the first display information generation unit 11 generates first display information for displaying, on the screen of the display device 30, a matching image 41 such as shown in FIG. 2, based on the acquired image. Thereafter, in step A1, the first display information generation unit 11 transmits the first display information to the display device 30.

Note that a configuration may be adopted in which only a frame image in which a feature is readily visible is used as the matching image. Also, a frame image in which a feature that was not visible until the orientation of the face changed is detected may be used as the matching image.

Also, the second display information generation unit 12 generates second display information for displaying, on the screen of the display device 30, a second display region for displaying a reference face development image, based on the three-dimensional data of the reference head (step A2). Specifically, in step A2, the second display information generation unit 12 acquires the three-dimensional data of the reference head from the storage device 21.

Then, in step A2, the second display information generation unit 12 generates a reference face development image using the three-dimensional data of the reference head. Then, in step A2, the second display information generation unit 12 generates second display information for displaying, on the screen of the display device 30, a reference face development image 43 such as shown in FIG. 2, based on the generated reference face development image. Thereafter, in step A2, the second display information generation unit 12 transmits the second display information to the display device 30.

Note that, in the case where a reference face development image is stored in the storage device 21, the second display information generation unit 12 may acquire the reference face development image directly from the storage device 21.

The order of the above-described processing of A1 and processing of step A2 may be reversed or the respective processing may be executed in parallel.

Next, the user interface display information generation unit 13 generates first user interface display information for displaying, on the screen of the display device 30, a first user interface for enabling the user to designated a feature region in the second display region with reference to the first display region (step A3).

Specifically, in step A3, the user interface display information generation unit 13 displays a user interface 40 such as shown in FIG. 2 as the first user interface to enable the user to designate a feature region on the reference face development image.

Note that the user may designate a plurality of feature regions on the reference face development image, while viewing one matching image. Also, the user may designate one or more feature regions on the reference face development image, while viewing a plurality of matching images (frame images) in which the face is oriented differently. For example, the user may designate one or more feature regions on the reference face development image, while viewing a plurality of matching images in which the face is oriented differently. This results in feature regions being positioned accurately, and enables the number of feature regions to be increased.

Furthermore, designation of a feature region may be performed automatically. In that case, the detection unit 64 automatically detects a feature region from an image, displayed on the screen of the display device 30, that includes the face of the person targeted for matching, and the association unit 65 automatically associates the position of the detected feature region with a corresponding position on the reference face development image.

Next, in the case where a feature region indicating a facial feature of the person targeted for matching visible on the skin surface of the person targeted for matching is designated, using the second display region, displayed on the screen of the display device 30, that is for displaying the reference face development image generated based on the three-dimensional data of the reference head, the generation unit 61 generates feature information relating to that feature region (step A4).

Specifically, in the case where one or more feature regions are designated on the reference face development image using the first user interface, the generation unit 61, in step A4, first, generates feature information for each designated feature region. Thereafter, in step A4, the generation unit 61 outputs the feature information to the matching unit 62.

In the example in FIG. 2, in the case where the feature region 52 is designated on the reference face development image 43 using the user interface 40, the generation unit 61 generates feature information of the designated feature region 52.

The matching unit 62 matches the feature information against matching information in which a matching-use face development image and matching-use feature region for each person registered in advance are associated with each other (step A5). Specifically, in step A5, the matching unit 62, first, acquires feature information from the generation unit 61. Then, in step A5, the matching unit 62 executes matching processing with reference to respective matching information stored in the storage device 21 using the acquired feature information, and calculates a matching result. Thereafter, in step A5, the matching unit 62 associates the matching information with the calculated matching result.

The selection unit 63 selects a person to serve as a candidate based on a matching result (step A6). Specifically, in step A6, the selection unit 63 selects matching information whose matching index is greater than or equal to a threshold value set in advance. Then, in step A6, the selection unit 63 outputs the selected matching information to the candidate face image display information generation unit 14.

In the case where the feature region designated using the first user interface is matched against matching information in which a matching-use face development image and matching-use feature region for each person registered in advance are associated with each other, and a candidate person is selected based on a matching result, the candidate face image display information generation unit 14 generates candidate face image display information for displaying, on the screen of the display device 30, the matching-use face development image corresponding to the selected candidate person together with the matching-use feature region (step A7).

Specifically, in the case where a candidate person is selected by the selection unit 63 based on a matching result of the matching unit 62, the candidate face image display information generation unit 14, in step A7, first, acquires, from the storage device 21, the matching information in which the matching-use face development image and matching-use feature region corresponding to the selected candidate person are associated with each other.

Then, in step A7, the candidate face image display information generation unit 14 generates candidate face image display information for displaying, on the screen of the display device 30, a matching-use face development image 71 and matching-use feature region 73 such as shown in window 72 in FIG. 4, based on the acquired matching information. Thereafter, the candidate face image display information generation unit 14 transmits the candidate face image display information to the display device 30.

Note that, in the case where there are a plurality of candidate persons, the matching-use face development images are displayed in order, according to the matching results. For example, the matching-use face development images are displayed in descending order of matching indices (scores) indicated by the matching results.

Next, the display device 30 acquires the candidate face image display information and displays a matching-use face development image 71 and matching-use feature region 73 such as shown in window 72 in FIG. 4 on the screen (step A8).

Effects of Example Embodiment

According to this example embodiment as described above, by the user viewing a matching image and designating a feature region on a reference face development image, matching support leading to specification of the person targeted for matching can be provided using the designated feature region, even if the person in the matching image is not facing forward.

Also, by the feature region being designated utilizing the reference face development image, the influence of the undulations of the face arising from a change in the face orientation can be reduced, thus enabling the feature region corresponding to the feature to be easily designated on the reference face development image by the user, even if the apparent position of the feature changes.

Also, a matching apparatus that extracts an image corresponding to a person from a frame image captured by an image capturing apparatus and executes matching using the extracted image may be coordinated with the matching support apparatus. In that case, if an image corresponding to the feature is detected from any of the frame images, the processing may be switched from a matching processing mode for performing matching using the matching apparatus to a matching support processing mode for providing matching support using the matching support apparatus.

Also, if it is judged that the person in the captured image is the same as a person registered in advance, the matching-use face development image and matching-use feature region corresponding to the person in the captured image may be edited, based on the feature of the person.

Also, if it is judged that the person in the captured image is not the same as a person registered in advance, the matching-use face development image and matching-use feature region corresponding to the person in the captured image may be edited, based on the feature showing the difference between the person in the captured image and the person registered in advance.

[Program]

A program in the example embodiment of the invention need only be a program for causing a computer to execute the processing from step A1 shown in FIG. 5. The matching support apparatus and matching support method of this example embodiment can be realized, by this program being installed on a computer and executed. In this case, a processor of the computer functions and performs processing as the first display information generation unit 11, the second display information generation unit 12, the user interface display information generation unit 13, the candidate face image display information generation unit 14, the generation unit 61, the matching unit 62, the selection unit 63, the detection unit 64 and the association unit 65.

Also, the program in this example embodiment may be executed by a computer system constructed from a plurality of computers. In this case, for example, the computers may each function as one of the first display information generation unit 11, the second display information generation unit 12, the user interface display information generation unit 13, the candidate face image display information generation unit 14, the generation unit 61, the matching unit 62, the selection unit 63, the detection unit 64 and the association unit 65.

Example Variation

Hereinafter, an example variation will be described with reference to FIGS. 6 to 11.

[System Configuration]

Figure 6:
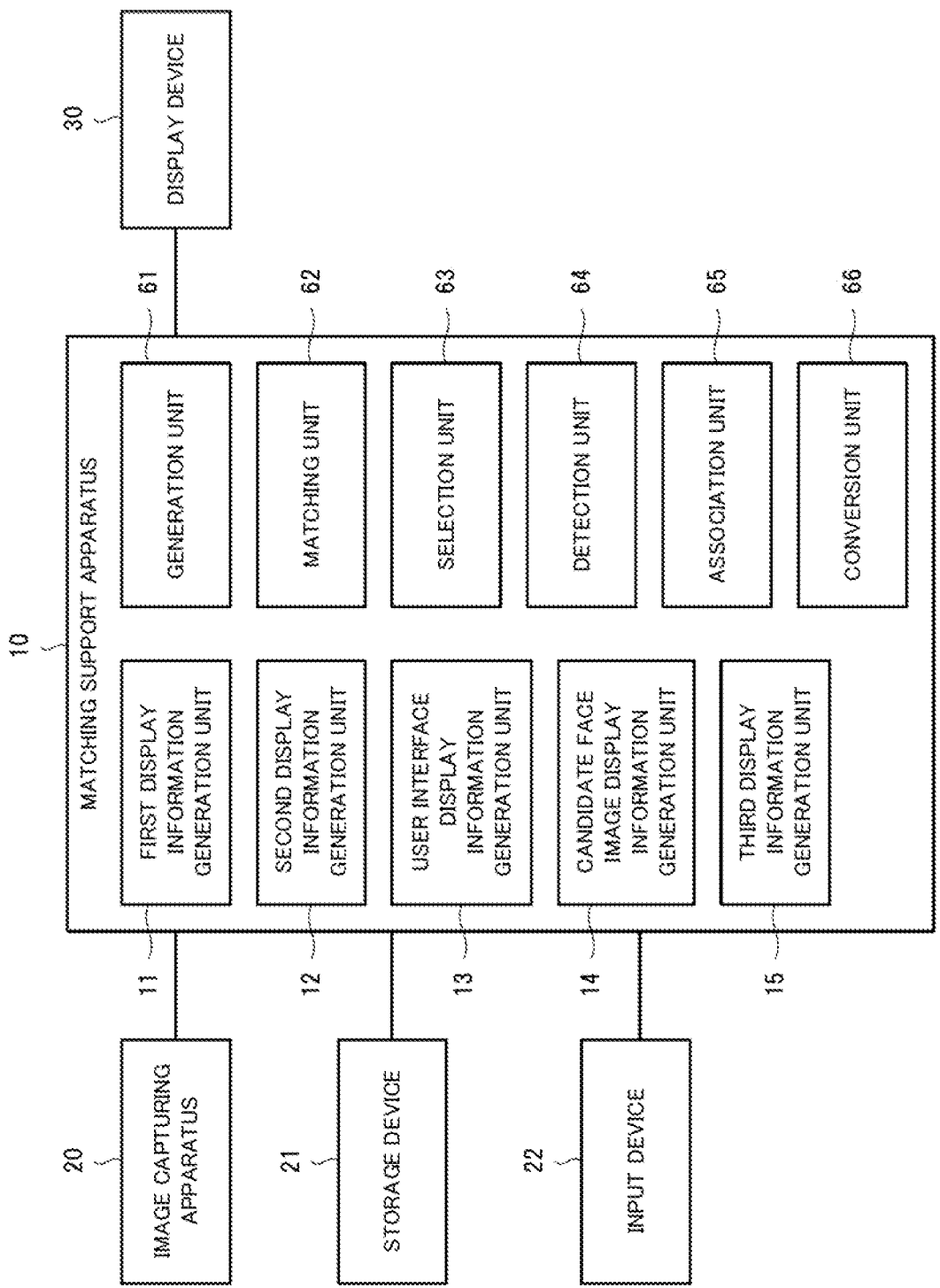
FIG. 6 is a diagram for describing an example of a system having the matching support apparatus.

The example variation will be described using FIG. 6. FIG. 6 is a diagram for describing an example of a system having the matching support apparatus.

As shown in FIG. 6, the matching support apparatus 10 in the example variation has a third display information generation unit 15 and a conversion unit 66, in addition to the first display information generation unit 11, the second display information generation unit 12, the user interface display information generation unit 13, the candidate face image display information generation unit 14, the generation unit 61, the matching unit 62, the selection unit 63, the detection unit 64 and the association unit 65.

In the example variation, in the case of further displaying a reference face three-dimensional image in a third display region, the storage device 21 transmits the three-dimensional data of the reference head to the matching support apparatus 10, via the communication network. The third display region will be described later. Note that, in the case where a reference face three-dimensional image is stored, the storage device 21 transmits the the reference face three-dimensional image to the matching support apparatus 10.

The third display information generation unit 15 generates third display information for displaying, on the screen of the display device 30, a third display region in which the face in a reference face three-dimensional image generated based on the three-dimensional data of the reference head is displayed to be oriented in alignment with the orientation of the face of the person targeted for matching that is displayed in the first display region. Specifically, the third display information generation unit 15 acquires the three-dimensional data of the reference head from the storage device 21.

Figure 7:
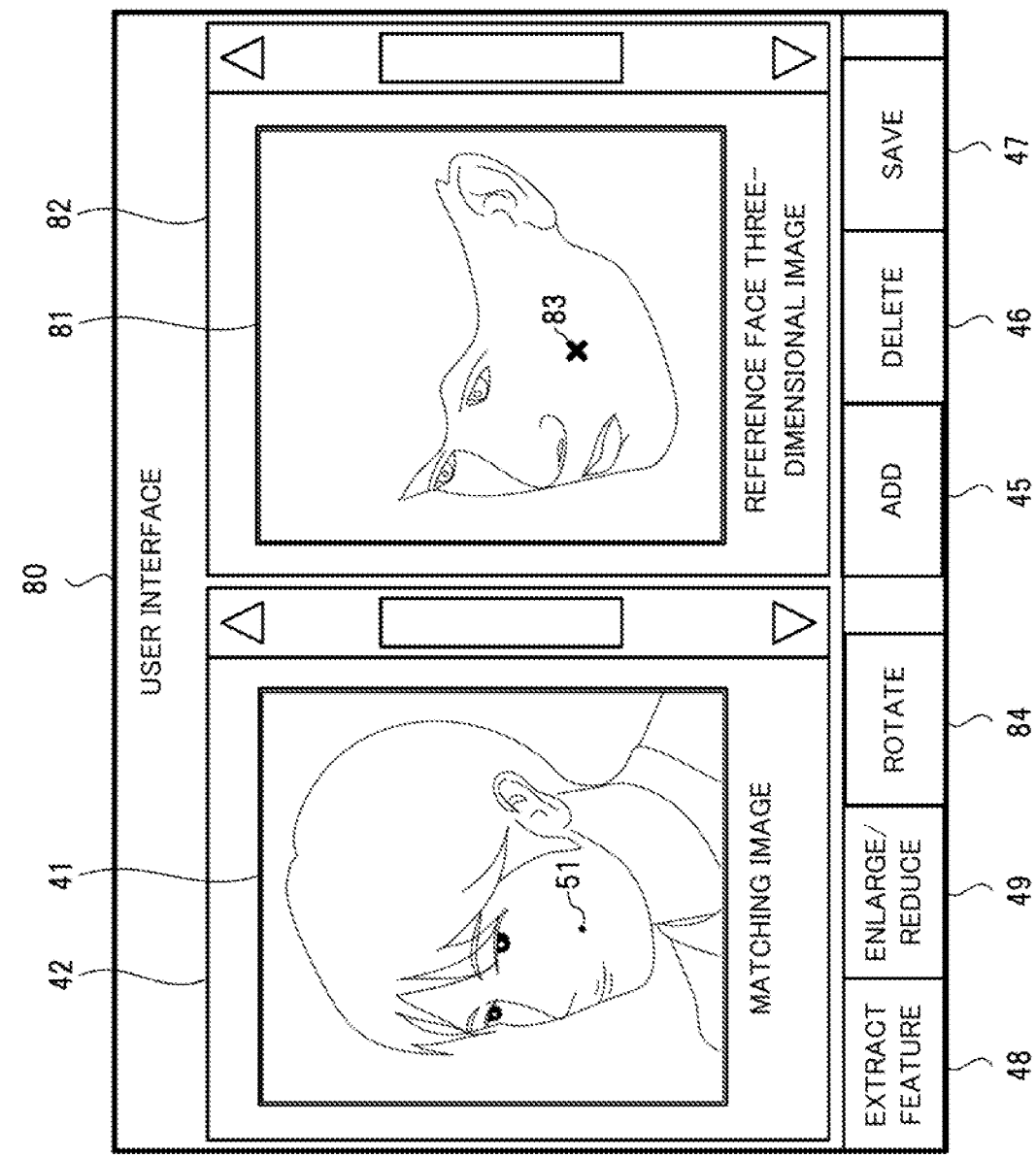
FIG. 7 is a diagram for describing a user interface that is used in matching support.

Then, the third display information generation unit 15 generates a reference face three-dimensional image using the three-dimensional data of the reference head. Then, the third display information generation unit 15 generates third display information for displaying, on the screen of the display device 30, a reference face three-dimensional image 81 such as shown in FIG. 7, based on the generated reference face three-dimensional image. Thereafter, the third display information generation unit 15 transmits the third display information to the display device 30. Note that, in the case where a reference face three-dimensional image is stored in the storage device 21, the third display information generation unit 15 may acquire the reference face three-dimensional image directly from the storage device 21.

Note that the orientation of the face may be manually aligned by the user using the user interface, or may be automatically aligned.

In the example variation, the user interface display information generation unit 13 generates second user interface display information for displaying, on the screen of the display device 30, a second user interface to be used in an operation for enabling the user to designate a feature region in the third display region.

A specific description will now be given using FIG. 7. FIG. 7 is a diagram for describing a user interface that is used in matching support.

The user interface display information generation unit 13 displays a user interface 80 such as shown in FIG. 7 as the second user interface to enable the user to designate a feature region on the reference face three-dimensional image. Note that, in the example in FIG. 7, the reference face three-dimensional image 81 is displayed in a window 82. The configuration of the display screen is, however, not limited to that in FIG. 7.

Note that the user may designate a plurality of feature regions on the reference face three-dimensional image, while viewing one matching image. Also, the user may designate one or more feature regions on the reference face three-dimensional image, while viewing a plurality of matching images (frame images) in which the face is oriented differently. For example, the user may designate one or more feature regions on the reference face three-dimensional image, while viewing a plurality of matching images in which the face is oriented differently. This results in feature regions being positioned accurately, and enables the number of feature regions to be increased.

Also, in the example variation, for example, when the "add" button 45 is selected after the user has selected the reference face three-dimensional image 81 shown in FIG. 7, a feature region 83 drawn on the reference face three-dimensional image 81 can be added. When the "delete" button 46 is selected, the feature region 83 drawn on the reference face three-dimensional image 81 can be deleted. When the "save" button 47 is selected, feature information (e.g., texture information, position information, feature type information, etc.) relating to the designated feature region 83 is stored in a storage unit. When the "extract feature" button 48 is selected, a feature is automatically extracted from the matching image 41. When the "enlarge/reduce" button 49 is selected, display of the matching image 41 or reference face development image 43 or reference face three-dimensional image 81 that is selected is enlarged or reduced. The editing functions are, however, not limited to the above-described functions.

In the example variation, in the case where a feature region indicating a facial feature of the person targeted for matching visible on the skin surface of the person targeted for matching is designated, using a third display region, displayed on the screen of the display device 30, that is for displaying a reference face three-dimensional image generated based on the three-dimensional data of the reference head, the generation unit 61 generates feature information relating to that feature region.

Specifically, in the case where one or more feature regions are designated on the reference face three-dimensional image using the second user interface, the generation unit 61, first, generates feature information for each designated feature region. Thereafter, the generation unit 61 outputs the feature information to the matching unit 62. In the example in FIG. 7, in the case where the feature region 83 is designated on the reference face three-dimensional image 81 using the user interface 80, the generation unit 61 generates feature information of the designated feature region 83.

In the case where a feature region is designated using the reference face three-dimensional image display region in which the face in the reference face three-dimensional image generated based on the three-dimensional data of the reference head is displayed to be oriented in alignment with the orientation of the face of the person targeted for matching, the conversion unit 66 converts the feature information relating to the feature region designated on the reference face three-dimensional image to feature information to be used with the reference face development image.

A description of the matching unit 62 and the selection unit 63 is given above and will thus be omitted here.

Figure 8:
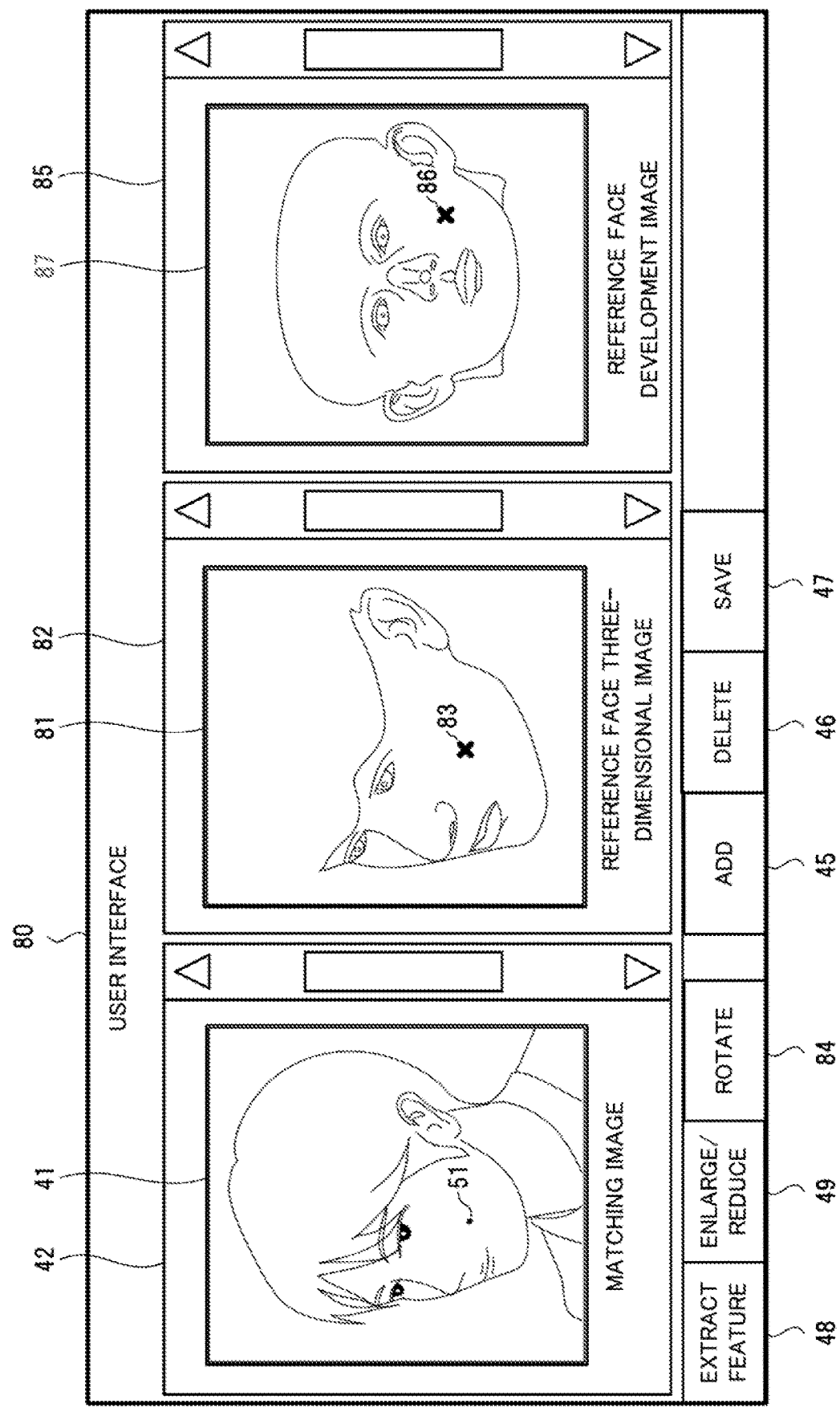
FIG. 8 is a diagram for describing an example of display in which a feature region on a reference face three-dimensional image is converted to a feature region on a face image in a reference face development image.

A specific description will now be given using FIG. 8. FIG. 8 is a diagram for describing an example of display in which a feature region on a reference face three-dimensional image is converted to a feature region on a face image in a reference face development image.

In FIG. 8, when the feature region 83 is added, a feature region 86 corresponding to the feature region 83 is also added to a reference face development image 87. Note that, in the example in FIG. 8, the reference face development image 87 is displayed in a window 85. The configuration of the display screen is, however, not limited to that in FIG. 8.

In the example variation, in the case where the feature region designated using the second user interface is matched against matching information in which a matching-use face development image and matching-use feature region for each person registered in advance are associated with each other, and a candidate person is selected based on a matching result, the candidate face image display information generation unit 14 generates candidate face image display information for displaying, on the screen of the display device 30, the matching-use face development image corresponding to the selected candidate together with the feature region.

Figure 9:
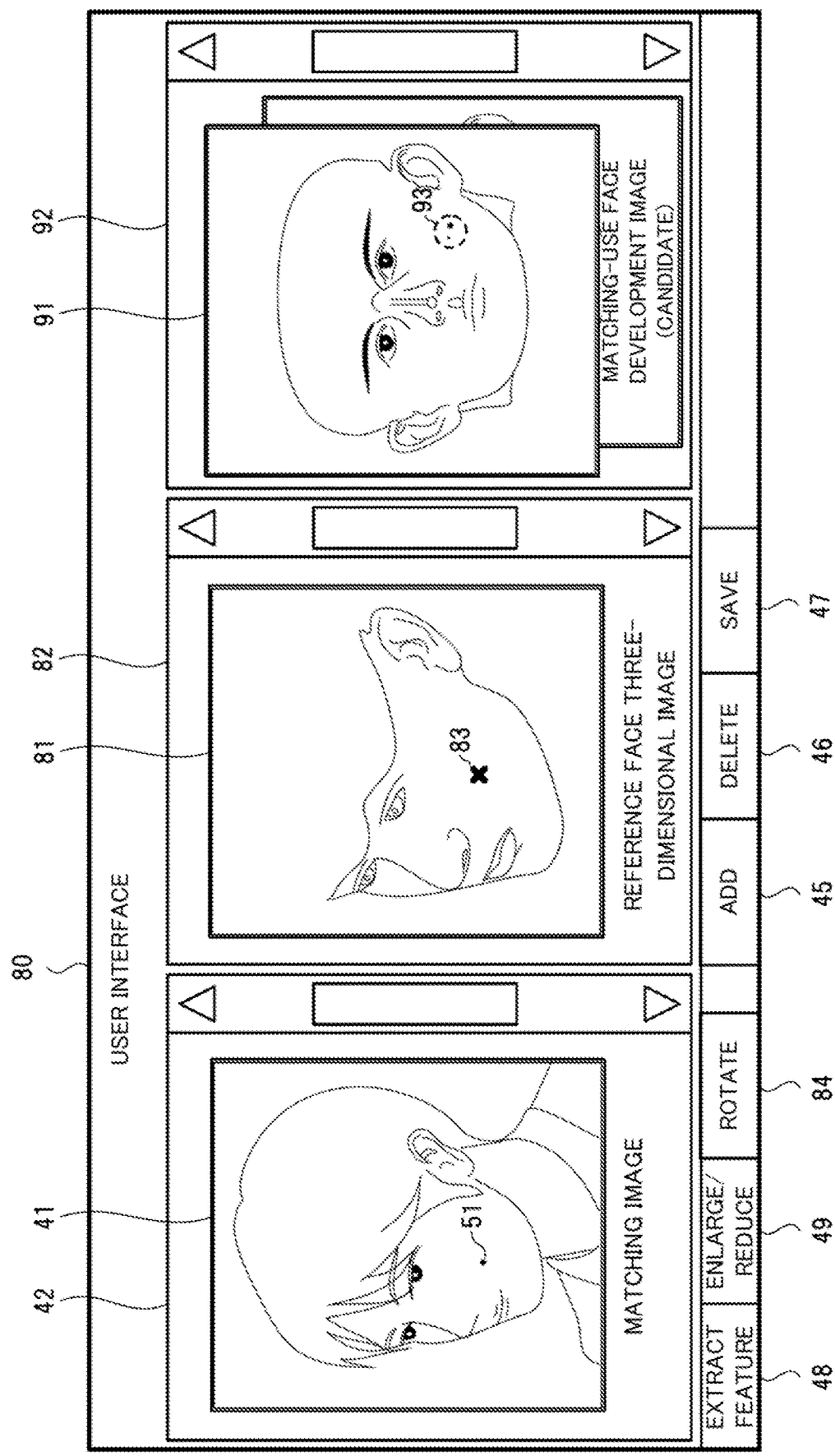
FIG. 9 is a diagram for describing an example of candidate face image display.

A specific description will now be given using FIG. 9. FIG. 9 is a diagram for describing an example of candidate face image display.

In the case where a candidate person is selected by the selection unit 63 based on a matching result of the matching unit 62, the candidate face image display information generation unit 14, first, acquires, from the storage device 21, the matching information in which the matching-use face development image and matching-use feature region corresponding to the selected candidate person are associated with each other.

Then, the candidate face image display information generation unit 14 generates candidate face image display information for displaying, on the screen of the display device 30, a matching-use face development image 91 and matching-use feature region 93 such as shown in a window 92 in FIG. 9, based on the acquired matching information. Thereafter, the candidate face image display information generation unit 14 transmits the candidate face image display information to the display device 30.

Note that, in the case where there are a plurality of candidate persons, the matching-use face development images are displayed in order, according to the matching results. For example, the matching-use face development images are displayed in descending order of matching indices (scores) indicated by the matching results.

Also, in the example variation, the candidate face image display information generation unit 14 generates candidate face three-dimensional image display information for displaying, on the screen of the display device 30, the matching-use face three-dimensional image corresponding to the candidate person, based on the three-dimensional data of the head of the selected candidate person.

Figure 10:
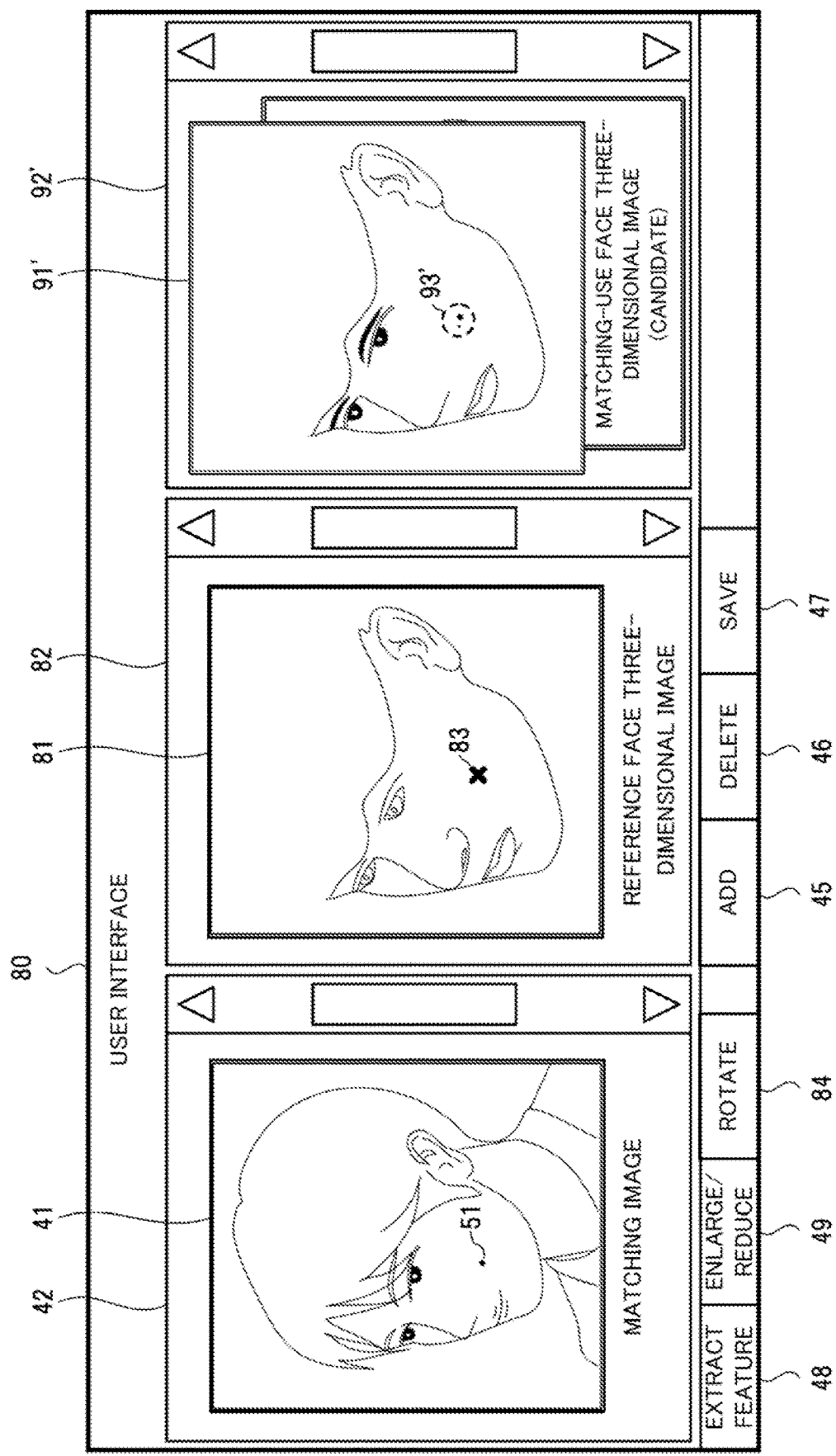
FIG. 10 is a diagram for describing an example of candidate face image display.

A specific description will now be given using FIG. 10. FIG. 10 is a diagram for describing an example of candidate face image display.

In the case where a candidate person is selected by the selection unit 63 based on a matching result of the matching unit 62, the candidate face image display information generation unit 14, first, acquires, from the storage device 21, the matching information in which the matching-use face three-dimensional image and matching-use feature region corresponding to the selected candidate person are associated with each other.

Then, the candidate face image display information generation unit 14 generates candidate face image display information for displaying, on the screen of the display device 30, a matching-use face three-dimensional image 91' and matching-use feature region 93' such as shown in a window 92' in FIG. 10, based on the acquired matching information. Thereafter, the candidate face image display information generation unit 14 transmits the candidate face image display information to the display device 30.

Note that one or more of the above-described matching image, reference face development image, reference face three-dimensional image, matching-use face development image including a matching-use feature region and matching-use face three-dimensional image including a matching-use feature region may be combined for display on the user interface.

[Apparatus Operations]

Figure 11:
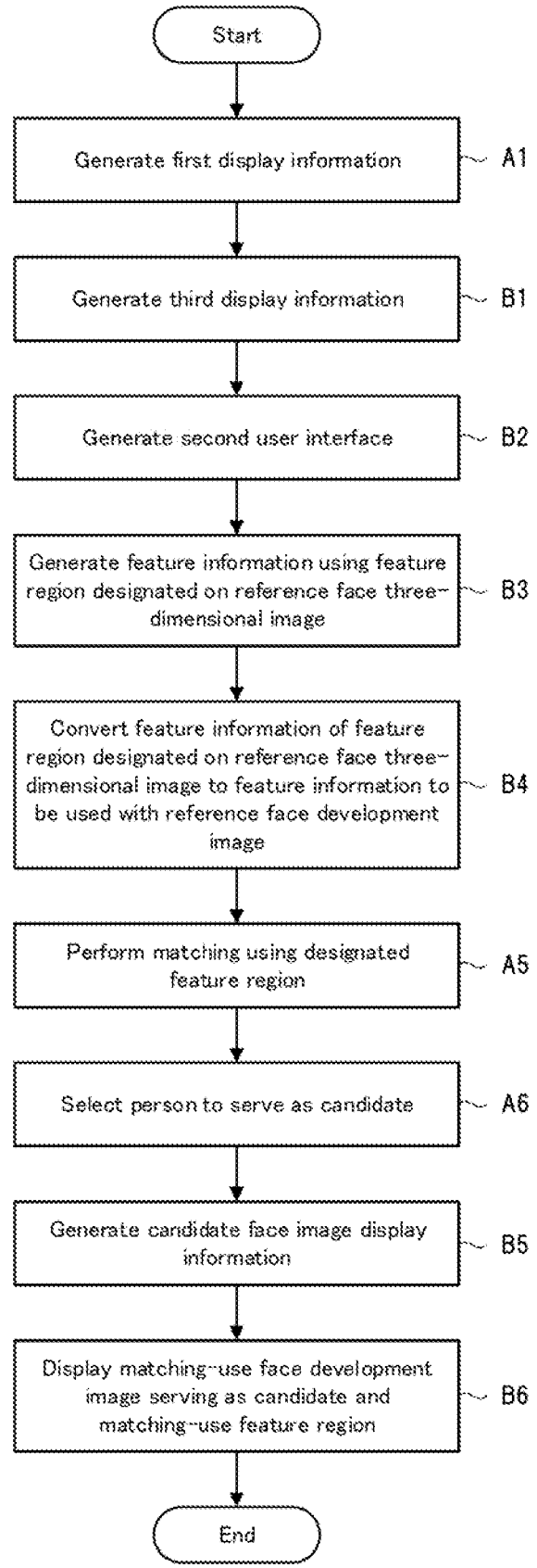
FIG. 11 is a diagram for describing an example of operations of the matching support apparatus.

Operations of the example variation will be described using FIG. 11. FIG. 11 is a diagram for describing an example of operations of the matching support apparatus. In the following description, FIGS. 1 to 10 will be referred to as appropriate. Also, in the example variation, a matching support method is implemented by operating the matching support apparatus. Therefore, the description of the matching support method in the example variation is replaced by the following description of the operations of the matching support apparatus.

As shown in FIG. 11, initially, the processing of step A1 described above is executed.

The third display information generation unit 15 generates third display information for displaying, on the screen of the display device 30, a third display region in which the face in a reference face three-dimensional image generated based on the three-dimensional data of the reference head is displayed to be oriented in alignment with the orientation of the face of the person targeted for matching that is displayed in the first display region (step B1). Specifically, the third display information generation unit 15 acquires the three-dimensional data of the reference head from the storage device 21.

Then, in step B1, the third display information generation unit 15 generates a reference face three-dimensional image using the three-dimensional data of the reference head. Then, in step B1, the third display information generation unit 15 generates third display information for displaying, on the screen of the display device 30, a reference face three-dimensional image 81 such as shown in FIG. 7, based on the generated reference face three-dimensional image. Thereafter, in step B1, the third display information generation unit 15 transmits the third display information to the display device 30.

Note that, in the case where a reference face three-dimensional image is stored in the storage device 21, the third display information generation unit 15 may acquire the reference face three-dimensional image directly from the storage device 21.

Note that the orientation of the face may be manually aligned by the user, or may be automatically aligned.

The order of the processing of step A1 and the processing of step B1 described above may be reversed, or the respective processing may be executed in parallel.

Next, the user interface display information generation unit 13 generates second user interface display information for displaying, on the screen of the display device 30, a second user interface to be used in an operation for enabling the user to designate a feature region in the third display region (step B2).

Specifically, in step B2, the user interface display information generation unit 13 displays a user interface 80 such as shown in FIG. 7 as the second user interface to enable the user to designate a feature region on the reference face three-dimensional image. Note that, in the example in FIG. 7, the reference face three-dimensional image 81 is displayed in the window 82. The configuration of the display screen is, however, not limited to that in FIG. 7.

Note that the user may designate a plurality of feature regions on the reference face three-dimensional image, while viewing one matching image. Also, the user may designate one or more feature regions on the reference face three-dimensional image, while viewing a plurality of matching images (frame images) in which the face is oriented differently. For example, the user may designate one or more feature regions on the reference face three-dimensional image, while viewing a plurality of matching images in which the face is oriented differently. This results in feature regions being positioned accurately and enables the number of feature regions to be increased, thus improving matching accuracy.

Furthermore, designation of a feature region may be performed automatically. In that case, the detection unit 64 automatically detects a feature region from an image, displayed on the screen of the display device 30, that includes the face of the person targeted for matching, and the association unit 65 automatically associates the position of the detected feature region with a corresponding position on the reference face three-dimensional image.

Next, in the case where a feature region indicating a facial feature of the person targeted for matching visible on the skin surface of the person targeted for matching is designated, using a third display region, displayed on the screen of the display device 30, that is for displaying the reference face three-dimensional image generated based on the three-dimensional data of the reference head, the generation unit 61 generates feature information relating to that feature region (step B3).

Specifically, in the case where one or more feature regions are designated on the reference face three-dimensional image, using the second user interface, the generation unit 61, in step B3, first, generates feature information for each designated feature region. Thereafter, in step B3, the generation unit 61 outputs the feature information to the matching unit 62. In the example in FIG. 7, in the case where the feature region 83 is designated on the reference face three-dimensional image 81 using the user interface 80, the generation unit 61 generates feature information of the designated feature region 83.

Next, in the case where a feature region is designated using the reference face three-dimensional image display region in which the face in the reference face three-dimensional image generated based on the three-dimensional data of the reference head is displayed to be oriented in alignment with the orientation of the face of the person targeted for matching, the conversion unit 66 converts the feature information relating to the feature region designated on the reference face three-dimensional image to feature information to be used with the reference face development image (step B4).

Next, the processing of steps A5 and A6 described above is executed.

Next, in the case where the feature region designated using the second user interface is matched against matching information in which a matching-use face development image and matching-use feature region for each person registered in advance are associated with each other, and a candidate person is selected based on a matching result, the candidate face image display information generation unit 14 generates candidate face image display information for displaying, on the screen of the display device 30, the matching-use face development image corresponding to the selected candidate together with the feature region (step B5).

In the case where a candidate person is selected by the selection unit 63 based on a matching result of the matching unit 62, the candidate face image display information generation unit 14, in step B5, first, acquires, from the storage device 21, the matching information in which the matching-use face development image and matching-use feature region corresponding to the selected candidate person are associated with each other.

Then, in step B5, the candidate face image display information generation unit 14 generates candidate face image display information for displaying, on the screen of the display device 30, a matching-use face development image 91 and matching-use feature region 93 such as shown in the window 92 in FIG. 9, based on the acquired matching information. Thereafter, the candidate face image display information generation unit 14 transmits the candidate face image display information to the display device 30.

Note that, in the case where there are a plurality of candidate persons, the matching-use face development images are displayed in order, according to the matching results. For example, the matching-use face development images are displayed in descending order of matching indices (scores) indicated by the matching results.

Also, in step B5, the candidate face image display information generation unit 14 may generate candidate face three-dimensional image display information for displaying, on the screen of the display device 30, the matching-use face three-dimensional image corresponding to the candidate person, based on the three-dimensional data of the head of the selected candidate person.

In the case where a candidate person is selected by the selection unit 63 based on a matching result of the matching unit 62, the candidate face image display information generation unit 14, in step B5, first, acquires, from the storage device 21, the matching information in which the matching-use face three-dimensional image and matching-use feature region corresponding to the selected candidate person are associated with each other.

Then, in step B5, the candidate face image display information generation unit 14 generates candidate face image display information for displaying, on the screen of the display device 30, a matching-use face three-dimensional image 91' and matching-use feature region 93' such as shown in the window 92' in FIG. 10, based on the acquired matching information. Thereafter, the candidate face image display information generation unit 14 transmits the candidate face image display information to the display device 30.

Note that, in the case where there are a plurality of candidate persons, the matching-use face development images are displayed in order, according to the matching results. For example, the matching-use face development images are displayed in descending order of matching indices (scores) indicated by the matching results.

Next, the display device 30 acquires the candidate face image display information and displays a matching-use face development image 91 and matching-use feature region 93 such as shown in the window 92 in FIG. 9 on the screen (step B6). Alternatively, in step B6, the display device 30 may display a matching-use face development image 91' and matching-use feature region 93' such as shown in the window 92' in FIG. 10 on the screen.

Effects of Variation

According to the example variation as described above, by the user viewing a matching image and designating a feature region on a reference face three-dimensional image, matching support leading to specification of the person targeted for matching can be provided using the designated feature region, even if the person in the matching image is not facing forward.

Also, by the feature region being designated utilizing the reference face three-dimensional image, the influence of the undulations of the face arising from a change in the face orientation can be reduced, thus enabling the feature region corresponding to the feature to be easily designated on the reference face three-dimensional image by the user, even if the apparent position of the feature changes.

Also, a matching apparatus that extracts an image corresponding to a person from a frame image captured by an image capturing apparatus and executes matching using the extracted image may be coordinated with the matching support apparatus. In that case, if an image corresponding to the feature is detected from any of the frame images, the processing may be switched from a matching processing mode for performing matching using the matching apparatus that is currently set to a matching support processing mode for providing matching support using the matching support apparatus.

Also, if it is judged that the person in the captured image is the same as a person registered in advance, the matching-use face development image and matching-use feature region corresponding to the person in the captured image may be edited, based on the feature of the person.

Also, if it is judged that the person in the captured image is not the same as a person registered in advance, the matching-use face development image and matching-use feature region corresponding to the person in the captured image may be edited, based on the feature showing the difference between the person in the captured image and the person registered in advance.

[Program]

A program in the example variation need only be a program for causing a computer to execute the processing from step A1 shown in FIG. 11. The matching support apparatus and matching support method of this example variation can be realized, by this program being installed on a computer and executed. In this case, a processor of the computer functions and performs processing as the first display information generation unit 11, the second display information generation unit 12, the user interface display information generation unit 13, the candidate face image display information generation unit 14, the third display information generation unit 15, the generation unit 61, the matching unit 62, the selection unit 63, the detection unit 64, the association unit 65 and the conversion unit 66.

Also, the program in this example variation may be executed by a computer system constructed from a plurality of computers. In this case, for example, the computers may each function as one of the first display information generation unit 11, the second display information generation unit 12, the user interface display information generation unit 13, the candidate face image display information generation unit 14, the third display information generation unit 15, the generation unit 61, the matching unit 62, the selection unit 63, the detection unit 64, the association unit 65 and the conversion unit 66.

[Physical Configuration]

Figure 12:
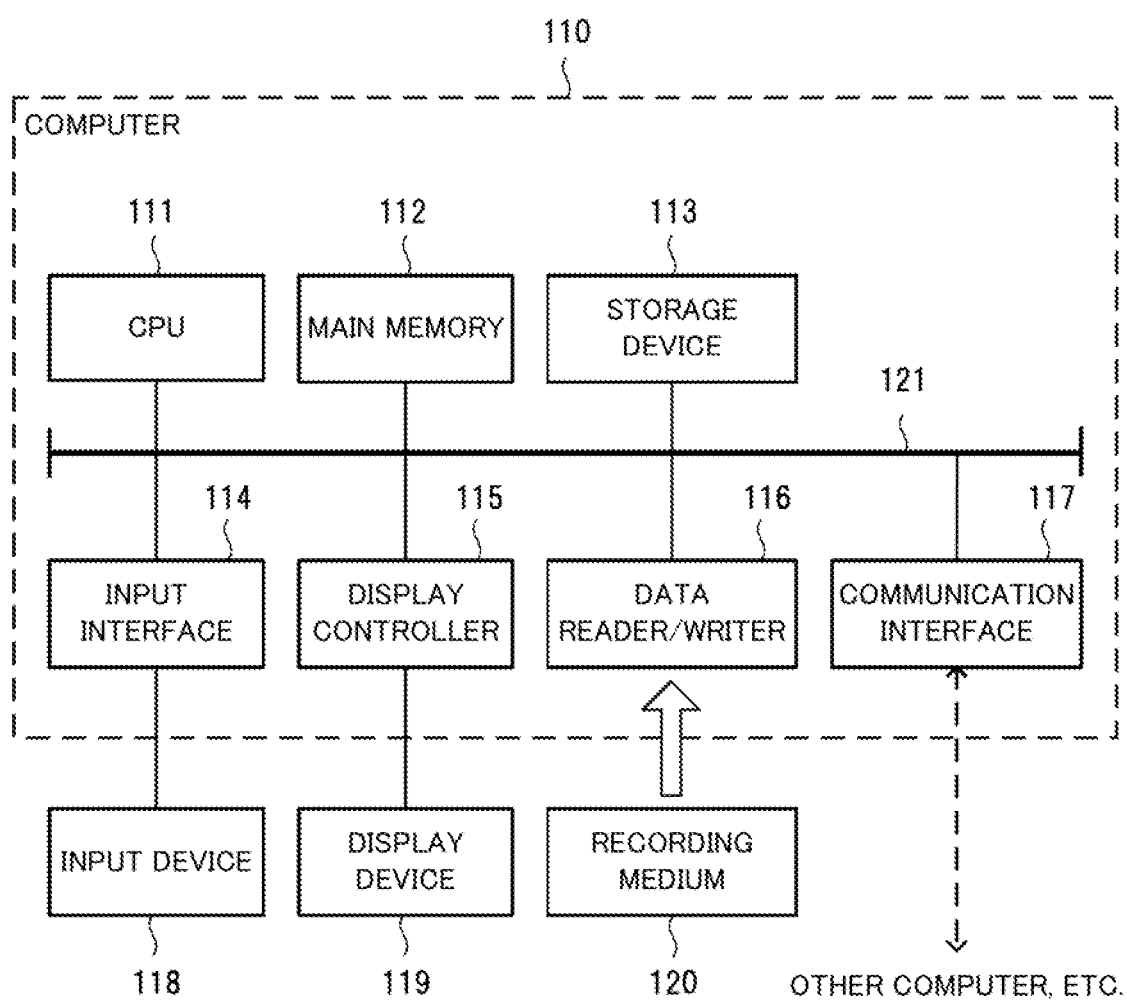
FIG. 12 is a diagram for describing an example of a computer that realizes the matching support apparatus.

Here, a computer that realizes the matching support apparatus by executing programs of the example embodiment and variation will be described using FIG. 12. FIG. 12 is a block diagram showing an example of a computer that realizes the matching support apparatus of the example embodiment and variation.

As shown in FIG. 12, a computer 110 includes a CPU 111, a main memory 112, a storage device 113, an input interface 114, a display controller 115, a data reader/writer 116 and a communication interface 117. These constituent elements are connected to each other in a data communicable manner via a bus 121. Note that the computer 110 may also include a GPU (Graphics Processing Unit) or FPGA, in addition to the CPU 111 or instead of the CPU 111.

The CPU 111 carries out various computational operations by extracting programs (code) of the example embodiment that are stored in the storage device 113 to the main memory 112 and executing these programs in predetermined order. The main memory 112 is typically a volatile storage device such as a DRAM (Dynamic Random Access Memory). Also, programs of the example embodiment are provided in a state of being stored in a computer-readable recording medium 120. Note that programs of the example embodiment may also be distributed over the Internet connected via the communication interface 117. Note that the recording medium 120 is a nonvolatile storage medium.

Also, specific examples of the storage device 113 include a semiconductor storage device such as a flash memory, in addition to a hard disk drive. The input interface 114 mediates data transmission between the CPU 111 and an input device 118 such as a keyboard and a mouse. The display controller 115 is connected to a display device 119 and controls display on the display device 119.

The data reader/writer 116 mediates data transmission between the CPU 111 and the recording medium 120, and executes readout of programs from the recording medium 120 and writing of processing results of the computer 110 to the recording medium 120. The communication interface 117 mediates data transmission between the CPU 111 and other computers.

Also, specific examples of the recording medium 120 include a general-purpose semiconductor storage device such as a CF (Compact Flash (registered trademark) card or SD (Secure Digital) card, a magnetic recording medium such as a flexible disk, and an optical recording medium such as a CD-ROM (Compact Disk Read Only Memory).

Note that the matching support apparatus in the example embodiment can also be realized by using hardware corresponding to the respective constituent elements, rather than by a computer on which programs are installed. Furthermore, the matching support apparatus may be partially realized by programs and the remaining portion thereof may be realized by hardware.

The following supplementary notes will be further disclosed in relation to the above example embodiment. The example embodiment described above can be partially or wholly realized by supplementary notes 1 to 18 described below, but the invention is not limited to the following description.

Supplementary Note 1

A matching support apparatus including:
a first display information generation unit configured to generate first display information for displaying, on a screen of a display device, a first display region for displaying an image including a face of a person targeted for matching captured using an image capturing apparatus;
a second display information generation unit configured to generate second display information for displaying, on the screen of the display device, a second display region for displaying a reference face development image generated based on three-dimensional data of a head serving as a reference; and
a user interface display information generation unit configured to generate first user interface display information for displaying, on the screen of the display device, a first user interface to be used in an operation for enabling a user to designate, in the second display region, a feature region indicating a facial feature of the person targeted for matching visible on a skin surface of the person targeted for matching.

Supplementary Note 2

The matching support apparatus according to supplementary note 1, including:
a candidate face image display information generation unit configured to, in a case where the feature region designated using the first user interface is matched against matching information in which a matching-use face development image and matching-use feature region for each person registered in advance are associated with each other, and a person to serve as a candidate is selected based on a matching result, generate candidate face image display information for displaying, on the screen of the display device, the matching-use face development image corresponding to the selected candidate person together with the matching-use feature region.

Supplementary Note 3

The matching support apparatus according to supplementary note 2, including:
a third display information generation unit configured to generate third display information for displaying, on the screen of the display device, a third display region in which a face in a reference face three-dimensional image generated based on the three-dimensional data of the reference head is displayed to be oriented in alignment with an orientation of the face of the person targeted for matching displayed in the first display region.

Supplementary Note 4

The matching support apparatus according to supplementary note 3,
whereby the user interface display information generation unit generates second user interface display information for displaying, on the screen of the display device, a second user interface to be used in an operation for enabling the user to designate the feature region in the third display region.

Supplementary Note 5

The matching support apparatus according to supplementary note 4,
whereby the candidate face image display information generation unit, in a case where the feature region designated using the second user interface is matched against matching information in which a matching-use face development image and matching-use feature region for each person registered in advance are associated with each other, and a person to serve as a candidate is selected based on a matching result, generates candidate face image display information for displaying, on the screen of the display device, the matching-use face development image corresponding to the selected candidate person together with the feature region.

Supplementary Note 6

The matching support apparatus according to any one of supplementary notes 2 to 5, whereby the candidate face image display information generation unit generates candidate face three-dimensional image display information for displaying, on the screen of the display device, a matching-use face three-dimensional image corresponding to the selected candidate person, based on three-dimensional data of a head of the selected candidate person.

Supplementary Note 7

A matching support method including:
(a) a step of generating first display information for displaying, on a screen of a display device, a first display region for displaying an image including a face of a person targeted for matching captured using an image capturing apparatus;
(b) a step of generating second display information for displaying, on the screen of the display device, a second display region for displaying a reference face development image generated based on three-dimensional data of a head serving as a reference; and
(c) a step of generating first user interface display information for displaying, on the screen of the display device, a first user interface to be used in an operation for enabling a user to designate, in the second display region, a feature region indicating a facial feature of the person targeted for matching visible on a skin surface of the person targeted for matching.

Supplementary Note 8

The matching support method according to supplementary note 7, including:
(d) a step of, in a case where the feature region designated using the first user interface is matched against matching information in which a matching-use face development image and matching-use feature region for each person registered in advance are associated with each other, and a person to serve as a candidate is selected based on a matching result, generating candidate face image display information for displaying, on the screen of the display device, the matching-use face development image corresponding to the selected candidate person together with the matching-use feature region.

Supplementary Note 9

The matching support method according to supplementary note 8, including:
(e) a step of generating third display information for displaying, on the screen of the display device, a third display region in which a face in a reference face three-dimensional image generated based on the three-dimensional data of the reference head is displayed to be oriented in alignment with an orientation of the face of the person targeted for matching displayed in the first display region.

Supplementary Note 10

The matching support method according to supplementary note 9, including:
(f) a step of generating second user interface display information for displaying, on the screen of the display device, a second user interface to be used in an operation for enabling the user to designate the feature region in the third display region.

Supplementary Note 11

The matching support method according to supplementary note 10, including:
(g) a step of, in a case where the feature region designated using the second user interface is matched against matching information in which a matching-use face development image and matching-use feature region for each person registered in advance are associated with each other, and a person to serve as a candidate is selected based on a matching result, generating candidate face image display information for displaying, on the screen of the display device, the matching-use face development image corresponding to the selected candidate person together with the feature region.

Supplementary Note 12

The matching support method according to any one of supplementary notes 8 to 11, including:
(h) a step of generating candidate face three-dimensional image display information for displaying, on the screen of the display device, a matching-use face three-dimensional image corresponding to the selected candidate person, based on three-dimensional data of a head of the selected candidate person.

Supplementary Note 13

A computer-readable recording medium that includes a program recorded thereon, the program including instructions that cause a computer to carry out:
(a) a step of generating first display information for displaying, on a screen of a display device, a first display region for displaying an image including a face of a person targeted for matching captured using an image capturing apparatus;
(b) a step of generating second display information for displaying, on the screen of the display device, a second display region for displaying a reference face development image generated based on three-dimensional data of a head serving as a reference; and
(c) a step of generating first user interface display information for displaying, on the screen of the display device, a first user interface to be used in an operation for enabling a user to designate, in the second display region, a feature region indicating a facial feature of the person targeted for matching visible on a skin surface of the person targeted for matching.

Supplementary Note 14

The computer-readable recording medium according to supplementary note 13, the program further including instructions that cause the computer to carry out:
(d) a step of, in a case where the feature region designated using the first user interface is matched against matching information in which a matching-use face development image and matching-use feature region for each person registered in advance are associated with each other, and a person to serve as a candidate is selected based on a matching result, generating candidate face image display information for displaying, on the screen of the display device, the matching-use face development image corresponding to the selected candidate person together with the matching-use feature region.

Supplementary Note 15

The computer-readable recording medium according to supplementary note 14, the program further including instructions that cause the computer to carry out:
(e) a step of generating third display information for displaying, on the screen of the display device, a third display region in which a face in a reference face three-dimensional image generated based on the three-dimensional data of the reference head is displayed to be oriented in alignment with an orientation of the face of the person targeted for matching displayed in the first display region.

Supplementary Note 16

The computer-readable recording medium according to supplementary note 15, the program further including instructions that cause the computer to carry out:
(f) a step of generating second user interface display information for displaying, on the screen of the display device, a second user interface to be used in an operation for enabling the user to designate the feature region in the third display region.

Supplementary Note 17

The computer-readable recording medium according to supplementary note 16, the program further including instructions that cause the computer to carry out:
(g) a step of, in a case where the feature region designated using the second user interface is matched against matching information in which a matching-use face development image and matching-use feature region for each person registered in advance are associated with each other, and a person to serve as a candidate is selected based on a matching result, generating candidate face image display information for displaying, on the screen of the display device, the matching-use face development image corresponding to the selected candidate person together with the feature region.

Supplementary Note 18

The computer-readable recording medium according to any one of supplementary notes 14 to 17, the program further including instructions that cause the computer to carry out:
(h) a step of generating candidate face three-dimensional image display information for displaying, on the screen of the display device, a matching-use face three-dimensional image corresponding to the selected candidate person, based on three-dimensional data of a head of the selected candidate person.

Although the application has been described above with reference to an example embodiment, the invention is not limited to the foregoing example embodiment. Various modifications that will be appreciated by those skilled in the art can be made to the configurations and details of the application within the scope of the application.

INDUSTRIAL APPLICABILITY

According to the application as described above, a feature visible on the skin surface of the face of a person targeted for matching can be designated, according to the orientation of the face in a captured image. The application is useful in fields that require matching such as monitoring systems and authentication systems.

LIST OF REFERENCE SIGNS

10 Matching support apparatus
11 First display information generation unit
12 Second display information generation unit
13 User interface display information generation unit
14 Candidate face image display information generation unit
15 Third display information generation unit
20 Image capturing apparatus
21 Storage device
22 Input device
30 Display device
61 Generation unit
62 Matching unit
63 Selection unit
64 Detection unit
65 Association unit
66 Conversion unit
110 Computer
111 CPU
112 Main memory
113 Storage device
114 Input interface
115 Display controller
116 Data reader/writer
117 Communication interface
118 Input device
119 Display device
120 Recording medium
121 Bus

What is claimed is:

1. A matching support apparatus comprising:
at least one memory storing instructions; and
at least one processor configured to execute the instructions to:
display, on a screen of a display device, a first display region for displaying a frame image of a still image or a moving image including a face of a person targeted for matching that is captured using an image capturing apparatus;
display, on the screen of the display device, a second display region for displaying a reference face development image created by CG (Computer Graphics) based on data of one or more heads measured or previously captured, on a screen of a display device;
when a facial feature visible is not visible on a skin surface of the person targeted for matching displayed in the first display region, display, on the screen of the display device, a first user interface to be used in an operation for enabling a user to designate, in the second display region, a feature region indicating the facial feature of the person targeted for matching that is visible on a skin surface of the person targeted for matching;
in a case where the feature region designated using the first user interface is matched against matching information in which a matching-use face development image and matching-use feature region for each person of a plurality of persons registered in advance are associated with each other, and in a case where a person of the plurality of persons is selected to serve as a candidate based on a matching result, display, on the screen of the display device, the matching-use face development image corresponding to the selected person together with the matching-use feature region; and
display, on the screen of the display device, a third display region in which a face in a reference face three-dimensional image generated based on three-dimensional data of a reference head is displayed to be oriented in alignment with an orientation of the face of the person targeted for matching displayed in the first display region,
wherein the facial feature of the person is at least any one or more of a mole, a freckle, a tattoo, a birthmark, a wrinkle, a dimple, a scar, a wart, a lump, rough skin, and a discolored skin patch, which is visible on the skin surface of the person.

2. The matching support apparatus according to claim 1, wherein the at least one processor is further configured to execute the instructions to:
display, on the screen of the display device, a second user interface to be used in an operation for enabling the user to designate the feature region in the third display region.

3. The matching support apparatus according to claim 2, wherein the at least one processor is further configured to execute the instructions to:
in a case where the feature region designated using the second user interface is matched against the matching information in which the matching-use face development image and the matching-use feature region for each person of the plurality of persons registered in advance are associated with each other, and in a case where the person is selected to serve as the candidate is selected based on the matching result, display, on the screen of the display device, the matching-use face development image corresponding to the selected person together with the feature region.

4. The matching support apparatus according to claim 1, wherein the at least one processor is further configured to execute the instructions to:
display, on the screen of the display device, a matching-use face three-dimensional image corresponding to the selected person, based on three-dimensional data of a head of the selected person.

5. A matching support method performed by a computer and comprising:
displaying, on a screen of a display device, a first display region for displaying a frame image of a still image or a moving image including a face of a person targeted for matching that is captured using an image capturing apparatus;
displaying, on the screen of the display device, a second display region for displaying a reference face development image created by CG (Computer Graphics) based on data of one or more heads measured or previously captured, on a screen of a display device;
when a facial feature visible is not visible on a skin surface of the person targeted for matching displayed in the first display region, displaying, on the screen of the display device, a first user interface to be used in an operation for enabling a user to designate, in the second display region, a feature region indicating the facial feature of the person targeted for matching that is visible on a skin surface of the person targeted for matching;
in a case where the feature region designated using the first user interface is matched against matching information in which a matching-use face development image and matching-use feature region for each person of a plurality of persons registered in advance are associated with each other, and in a case where a person of the plurality of persons is selected to serve as a candidate based on a matching result, displaying, on the screen of the display device, the matching-use face development image corresponding to the selected person together with the matching-use feature region; and display, on the screen of the display device, a third display region in which a face in a reference face three-dimensional image generated based on three-dimensional data of a reference head is displayed to be oriented in alignment with an orientation of the face of the person targeted for matching displayed in the first display region, wherein the facial feature of the person is at least any one or more of a mole, a freckle, a tattoo, a birthmark, a wrinkle, a dimple, a scar, a wart, a lump, rough skin, and a discolored skin patch, which is visible on the skin surface of the person.

6. The matching support method according to claim 5, further comprising:

displaying, on the screen of the display device, a second user interface to be used in an operation for enabling the user to designate the feature region in the third display region.

7. The matching support method according to claim 6, further comprising:

in a case where the feature region designated using the second user interface is matched against the matching information in which the matching-use face development image and the matching-use feature region for each person of the plurality of persons registered in advance are associated with each other, and in a case where the person is selected to serve as the candidate is selected based on the matching result, displaying, on the screen of the display device, the matching-use face development image corresponding to the selected person together with the feature region.

8. The matching support method according to claim 5, further comprising:

displaying, on the screen of the display device, a matching-use face three-dimensional image corresponding to the selected person, based on three-dimensional data of a head of the selected person.

9. A non-transitory computer-readable recording medium storing a program executable by a computer to perform processing comprising:

displaying, on a screen of a display device, a first display region for displaying a frame image of a still image or a moving image including a face of a person targeted for matching that is captured using an image capturing apparatus;

displaying, on the screen of the display device, a second display region for displaying a reference face development image created by CG (Computer Graphics) based on data of one or more heads measured or previously captured, on a screen of a display device;

when a facial feature visible is not visible on a skin surface of the person targeted for matching displayed in the first display region, displacing, on the screen of the display device, a first user interface to be used in an operation for enabling a user to designate, in the second display region, a feature region indicating the facial feature of the person targeted for matching that is visible on a skin surface of the person targeted for matching;

in a case where the feature region designated using the first user interface is matched against matching information in which a matching-use face development image and matching-use feature region for each person of a plurality of persons registered in advance are associated with each other, and in a case where a person of the plurality of persons is selected to serve as a candidate based on a matching result, displaying, on the screen of the display device, the matching-use face development image corresponding to the selected person together with the matching-use feature region; and display, on the screen of the display device, a third display region in which a face in a reference face three-dimensional image generated based on three-dimensional data of a reference head is displayed to be oriented in alignment with an orientation of the face of the person targeted for matching displayed in the first display region, wherein the facial feature of the person is at least any one or more of a mole, a freckle, a tattoo, a birthmark, a wrinkle, a dimple, a scar, a wart, a lump, rough skin, and a discolored skin patch, which is visible on the skin surface of the person.

10. The non-transitory computer-readable recording medium according to claim 9, wherein the processing further comprises:

displaying, on the screen of the display device, a second user interface to be used in an operation for enabling the user to designate the feature region in the third display region.

11. The non-transitory computer-readable recording medium according to claim 10, wherein the processing further comprises:

in a case where the feature region designated using the second user interface is matched against the matching information in which the matching-use face development image and the matching-use feature region for each person of the plurality of persons registered in advance are associated with each other, and in a case where the person is selected to serve as the candidate is selected based on the matching result, displaying, on the screen of the display device, the matching-use face development image corresponding to the selected person together with the feature region.

12. The non-transitory computer-readable recording medium according to claim 9, wherein the processing further comprises:

displaying, on the screen of the display device, a matching-use face three-dimensional image corresponding to the selected person, based on three-dimensional data of a head of the selected person.

* * * * *

UNITED STATES PATENT AND TRADEMARK OFFICE
CERTIFICATE OF CORRECTION

| | | |
|---|---|---|
| PATENT NO. | : 12,260,604 B2 | Page 1 of 1 |
| APPLICATION NO. | : 17/636142 | |
| DATED | : March 25, 2025 | |
| INVENTOR(S) | : Yasushi Hamada | |

It is certified that error appears in the above-identified patent and that said Letters Patent is hereby corrected as shown below:

On the Title Page

Item (22)
Delete "(22) PCT Filed: Oct. 13, 2019"
Insert --(22) PCT Filed: Oct. 30, 2019--

Signed and Sealed this
Tenth Day of June, 2025

Coke Morgan Stewart
*Acting Director of the United States Patent and Trademark Office*